United States Patent
Leduc et al.

(10) Patent No.: US 8,066,782 B2
(45) Date of Patent: Nov. 29, 2011

(54) AZOMETHINE DIRECT DYES OR REDUCED PRECURSORS OF AZOMETHINE DIRECT DYES OBTAINED FROM 2-ALKYLRESORCINOLS, AND HAIR DYEING PROCESS USING THESE DYES OR PRECURSORS

(75) Inventors: Madeleine Leduc, Paris (FR); Eric Metais, St Leu la Forêt (FR); Stéphane Sabelle, Paris (FR); Christophe Rondot, Mitry-mory (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/808,134

(22) PCT Filed: Dec. 9, 2008

(86) PCT No.: PCT/EP2008/067150
§ 371 (c)(1),
(2), (4) Date: Nov. 12, 2010

(87) PCT Pub. No.: WO2009/077391
PCT Pub. Date: Jun. 25, 2009

(65) Prior Publication Data
US 2011/0041263 A1     Feb. 24, 2011

Related U.S. Application Data

(60) Provisional application No. 61/006,277, filed on Jan. 4, 2008.

(30) Foreign Application Priority Data

Dec. 14, 2007   (FR) ..................................... 07 59851

(51) Int. Cl.
*A61Q 5/10*     (2006.01)

(52) U.S. Cl. ............. 8/405; 8/406; 8/410; 8/426; 8/435; 8/462

(58) Field of Classification Search .............. 8/405, 406, 8/410, 426, 435, 462
See application file for complete search history.

(56) References Cited

U.S. PATENT DOCUMENTS 4,361,516 A    11/1982   Kalopisis et al.
6,530,960 B1    3/2003   Pastore et al.

FOREIGN PATENT DOCUMENTS

EP    1 093 792 A1    4/2001
FR    2 254 557    7/1975

OTHER PUBLICATIONS

STIC Search Report dated Mar. 14, 2011.*
A. Bonnet et al., "<<Trinoyaux>>. Détermination des structures par RMN $^1$H, $^{13}$C et $^{15}$N," Journal de Chimie Physique, vol. 92, pp. 1823-1828 (1995).
International Search Report for PCT/EP2008/067150, dated May 27, 2009.

* cited by examiner

*Primary Examiner* — Eisa Elhilo
(74) *Attorney, Agent, or Firm* — Finnegan, Henderson, Farabow, Garrett & Dunner, L.L.P.

(57) ABSTRACT

The invention relates to the dyeing of keratin fibres using azomethine direct dyes or precursors of azomethine dyes obtained from 2-alkylresorcinols. The invention relates to a dye composition comprising at least one azomethine direct dye or pre-cursor of an azomethine direct dye, to a process for dyeing keratin fibres, using the said composition, and to their uses in the dyeing of keratin fibres. This composition allows a particularly stable and fast coloration to be obtained.

19 Claims, No Drawings

AZOMETHINE DIRECT DYES OR REDUCED PRECURSORS OF AZOMETHINE DIRECT DYES OBTAINED FROM 2-ALKYLRESORCINOLS, AND HAIR DYEING PROCESS USING THESE DYES OR PRECURSORS

CROSS REFERENCE TO RELATED APPLICATIONS

This application is a national phase application based on PCT/EP2008/067150, filed Dec. 9, 2008, which claims the priority of French Patent Application No. 0759851, filed Dec. 14, 2007; and claims the benefit of U.S. Provisional Application No. 61/006,277, filed Jan. 4, 2008; the content of all of which is incorporated herein by reference.

The invention relates to the dyeing of keratin fibres using azomethine direct dyes or reduced precursors of azomethine direct dyes obtained from 2-alkyl-resorcinols.

It is known practice to dye keratin fibres, and in particular the hair, with dye compositions containing direct dyes, according to a "direct dyeing" process.

The process conventionally used in direct dyeing consists in applying to keratin fibres direct dyes, or colouring molecules, which have affinity for the said fibres, leaving them to stand on the fibres, and then rinsing the fibres. The direct dyes used hitherto are nitrobenzene dyes, anthraquinones, nitropyridines, dyes of azo, xanthene, acridine or azine type or triarylmethanebenzene-based dyes.

Other dyes are obtained from oxidation bases and oxidation couplers, which, once condensed, are applied onto the hair. For example, in documents FR 233 036, FR 2 262 022, FR 2 262 024, U.S. Pat. No. 4 221 729 and FR 2 261 750, diphenylamines such as leuco derivatives of indophenols, of indoamine and of indoaniline are used either alone or in combination with other dyes in dye compositions. Other compounds corresponding to oxidized derivatives of leuco derivatives such as those described in documents FR 2 254 557 and FR 2 234 277 are also known for dyeing keratin fibres. None of these dyes are derivatives originating from 2-alkylresorcinol derivatives.

The colorations that result from direct dyeing are temporary or semi-permanent colorations, since the nature of the interactions that bind the direct dyes to the keratin fibre, and their desorption from the surface and/or the core of the fibre, are responsible for their poor dyeing power and their poor fastness with respect to washing or to perspiration. These direct dyes are also generally sensitive to the action of oxidizing agents such as hydrogen peroxide, which makes them generally unusable in lightening direct dye compositions based on hydrogen peroxide and on a basifying agent, which would be similar to oxidation dyeing.

Direct dyes also have a certain lack of light stability, associated with the poor resistance of the chromophore to photochemical attack. In addition, their sensitivity to light is dependent on the distribution of their molecules, uniformly or in aggregates, in the substrate.

Consequently, there is a real need to find direct dyes for dyeing keratin fibres, which are light-stable, and which are also resistant to bad weather, washing and perspiration and sufficiently stable in the presence of oxidizing agents such as hydrogen peroxide to be able to obtain simultaneous lightening of the fibre with the advantages outlined above, while at the same time having a toxicological profile that is improved and compatible with cosmetic use on keratin fibres.

These aims are achieved with the present invention, one subject of which is a process for dyeing keratin fibres using direct dyes of formula (I):

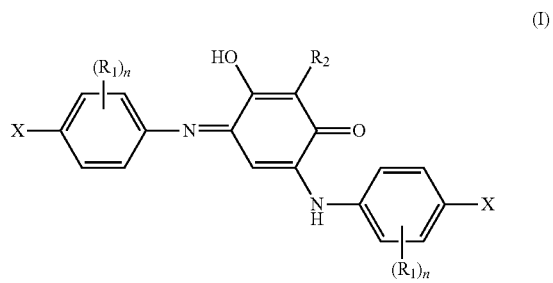

salts thereof with an organic or mineral acid, geometrical isomers thereof, tautomers thereof, and solvates thereof such as the hydrates; in which formula (I):

$R_1$, which may be identical or different, represent:
  a chlorine atom;
  a $(C_1-C_3)$alkyl radical optionally substituted with one or more hydroxyl groups;
  a $(C_1-C_3)$alkoxy radical optionally substituted with one or more hydroxyl groups;

$R_2$ represents a $(C_1-C_3)$alkyl radical;

X, which may be identical or different, represent:
  a hydroxyl radical;
  a radical —$NR_3R_4$ with $R_3$ and $R_4$ representing, independently of each other:
    i) a hydrogen atom;
    ii) a $C_1-C_5$ alkyl radical optionally substituted with one or more groups chosen from hydroxyl, $(C_1-C_3)$ alkoxy, amino, $(C_1-C_3)$ alkylamino, di$(C_1-C_3)$ alkylamino, aminocarbonyl, carboxylic —COOH, sulfonic —$SO_3H$, tri$(C_1-C_3)$alkylammonium and $(C_1-C_3)$ alkylimidazolium;
  a pyrrolidinyl radical optionally substituted with a group chosen from hydroxyl, $(C_1-C_3)$alkoxy, amino, $(C_1-C_3)$alkylamino, di$(C_1-C_3)$alkylamino, tri$(C_1-C_3)$ alkylammonium and $(C_1-C_3)$ alkylimidazolium;
  a piperidine radical optionally substituted with a group chosen from hydroxyl, $(C_1-C_3)$alkoxy, amino, $(C_1-C_3)$alkylamino, di$(C_1-C_3)$alkylamino, tri$(C_1-C_3)$ alkylammonium and $(C_1-C_3)$alkylimid-azolium;

n represents an integer between 0 and 3 inclusive;

it being understood that when X and/or $R_3$ and/or $R_4$ comprise a cationic group, the electrical neutrality of the compounds of formula (I) is achieved with an anionic counterion or a mixture of anionic counterions that are cosmetically acceptable, for instance chlorides, bromides and sulfates.

Another subject of the invention relates to a dyeing process using reduced precursors of colourless azomethine dyes, which, once oxidized, generate the compounds of formula (I) as defined above. These precursors correspond to the compounds of formula (II):

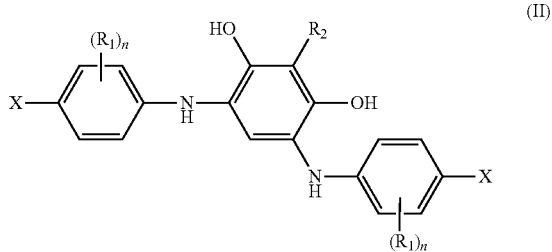

(II)

the salts thereof with an organic or mineral acid, the geometrical isomers thereof, the tautomers thereof, and the solvates thereof such as the hydrates;

in which formula (II) $R_1$, $R_2$, X and n are as defined previously;

it being understood that:

when X and/or $R_3$ and/or $R_4$ comprise a cationic group, the electrical neutrality of the compounds of formula (II) is achieved with an anionic counterion or a mixture of anionic counterions that are cosmetically acceptable, for instance chlorides, bromides and sulfates.

Another subject of the invention is a compound of formula (I) or (II) as defined previously.

Another subject of the invention is a dye composition for dyeing keratin fibres, comprising, in a cosmetic medium, at least one compound of formula (I) or (II) as defined previously.

The direct dyes of formula (I) make it possible to overcome the drawbacks of the direct dyes conventionally used previously, and lead to dyeing results by direct dyeing that show very good resistance to light, bad weather, perspiration and rubbing. Their good stability with respect to oxidizing agents such as hydrogen peroxide also allows them to be used in a process of lightening direct dyeing.

Furthermore, it has been discovered that the reduced form of the azomethine derivatives obtained from 2-alkylresorcinol derivatives of formula (II), used under oxidizing conditions, may also lead to colorations that show very good resistance to light, bad weather, washing, perspiration and rubbing.

For the purposes of the present invention, and unless otherwise indicated:

a "salt of an organic or mineral acid" is chosen, for example, from a solvent derived from i) hydrochloric acid HCl, ii) hydrobromic acid HBr, iii) sulfuric acid $H_2SO_4$, iv) alkylsulfonic acids: Alk-S(O)$_2$OH such as methanesulfonic acid and ethanesulfonic acid; v) arylsulfonic acids: Ar—S(O)$_2$OH such as benzenesulfonic acid and toluenesulfonic acid; vi) citric acid; vii) succinic acid; viii) tartaric acid; ix) lactic acid; x) alkoxysulfinic acids: Alk-O—S(O)OH such as methoxysulfinic acid and ethoxysulfinic acid; xi) aryloxysulfinic acids such as tolueneoxysulfinic acid and phenoxysulfinic acid; xii) phosphoric acid $H_3PO_4$; xiii) acetic acid $CH_3C(O)OH$; xiv) triflic acid $CF_3SO_3H$; and xv) tetrafluoroboric acid $HBF_4$;

an "anionic counterion" is an anion or an anionic group associated with the cationic charge of the dye; more particularly, the anionic counterion is chosen from: i) halides such as chloride or bromide; ii) nitrates; iii) sulfonates, including $C_1$-$C_6$ alkylsulfonates: Alk-S(O)$_2$O$^-$ such as methanesulfonate or mesylate and ethanesulfonate;

iv) arylsulfonates: Ar—S(O)$_2$O$^-$ such as benzenesulfonate and toluenesulfonate or tosylate;

v) citrate; vi) succinate; vii) tartrate; viii) lactate; ix) alkyl sulfates: Alk-O—S(O)O$^-$ such as methyl sulfate and ethyl sulfate; x) aryl sulfates: Ar—O—S(O)O$^-$ such as benzene sulfate and toluene sulfate; xi) alkoxy sulfates: Alk-O—S(O)$_2$O$^-$ such as methoxy sulfate and ethoxy sulfate; xii) aryloxy sulfates: Ar—O—S(O)$_2$O$^-$; xiii) phosphate;

xiv) acetate; xv) triflate; and xvi) borates such as a tetrafluoroborate;

an "alkyl" radical is a saturated, linear or branched hydrocarbon-based radical, containing from 1 to 6 carbon atoms and particularly from 1 to 3 carbon atoms, such as the methyl or ethyl radical;

an "alkoxy" radical is an "alkyl-oxy" alkyl-O -radical in which the alkyl part is as defined previously;

the alkyl, alkoxy or heterocycloalkyl radicals followed by "optionally substituted with . . . " means that the said radicals may have one or more hydrogen atoms replaced with one or more substituents in question, particularly one or two substituents in question.

One subject of the invention concerns direct dyes of formula (I) or dye precursors of formula (II).

One particular embodiment of the invention concerns the compounds of formula (I) or (II) for which n is zero.

According to another particular embodiment of the invention, the compound(s) of formula (I) or (II) contained in the composition according to the invention is (are) such that n is 1 and $R_1$ represents a ($C_1$-$C_3$)alkyl group such as methyl.

One variant concerns compounds of formula (I) or (II) for which X represents a hydroxyl radical.

Another variant of the invention involves compounds of formula (I) or (II) for which X represents a radical —NR$_3$R$_4$ with R$_3$ and R$_4$ representing, independently of each other, i) a hydrogen atom or ii) a $C_1$-$C_5$ alkyl radical optionally substituted with one or more groups chosen from hydroxyl, ($C_1$-$C_3$)alkoxy, amino, ($C_1$-$C_3$)alkylamino, di($C_1$-$C_3$)alkylamino, aminocarbonyl, carboxylic —COOH, sulfonic —SO$_3$H, tri ($C_1$-$C_3$)alkyl-ammonium and ($C_1$-$C_3$)alkylimidazolium. More particularly, X represents a group chosen from: i) (di) ($C_1$-$C_3$) (alkyl)amino; ii) (di) [hydroxy($C_1$-$C_3$)alkyl]amino; iii) ($C_1$-$C_3$)alkylimidazolium($C_1$-$C_3$)alkylamino; iv) [N-($C_1$-$C_3$)alkyl,N-($C_1$-$C_3$)alkylimidazolium($C_1$-$C_3$)alkyl]amino; v) tri($C_1$-$C_3$)alkylammonium($C_1$-$C_5$)alkylamino and vi) (di) [tri($C_1$-$C_3$)alkylammonium($C_1$-$C_5$)alkyl]amino.

According to another particular embodiment of the invention, the composition contains one or more compounds of formula (I) or (II) for which X represents a pyrrolidinyl group optionally substituted with a tri($C_1$-$C_3$)alkylammonium or ($C_1$-$C_3$)alkylimidazolium group. More particularly, X represents a pyrrolidino radical optionally substituted with a tri ($C_1$-$C_3$)alkylammonium or ($C_1$-$C_3$)alkylimidazolium group.

As examples of compounds of formula (I) or (II) contained in the composition according to the invention, mention may be made of the dyes (1a) to (1j) and precursors (2a) to (2j) below, and also the salts thereof with an organic or mineral acid, geometrical isomers thereof, tautomers thereof and solvates thereof such as the hydrates:

Dyes of formula (I):

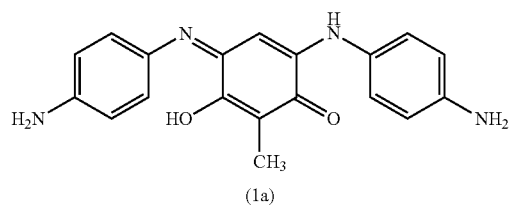
(1a)

6-(4-Aminophenylamino)-4-(4-aminophenylimino)-3-hydroxy-2-methylcyclohexa-2,5-dienone

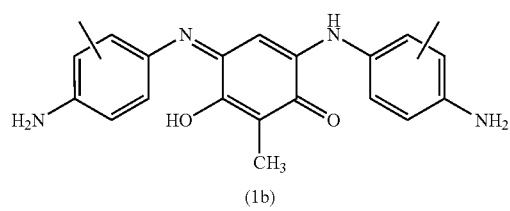
(1b)

6-(4-Aminomethylphenylamino)-4-(4-aminomethylphenylimino)-3-hydroxy-2-methylcyclohexa-2,5-dienone

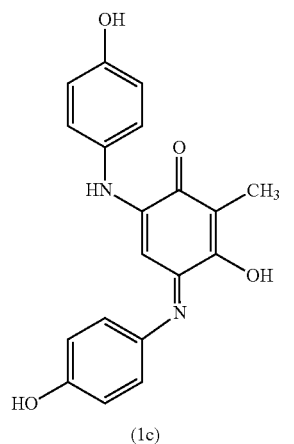
(1c)

3-Hydroxy-6-(4-hydroxy-phenylamino)-4-(4-hydroxy-phenylimino)-2-methylcyclohexa-2,5-dienone

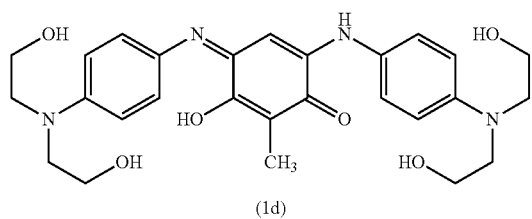
(1d)

6-{4-[Bis(2-hydroxyethyl)amino]-phenylamino}-4-{4-[bis(2-hydroxy-ethyl)amino]phenylimino}-3-hydroxy-2-methylcyclohexa-2,5-dienone

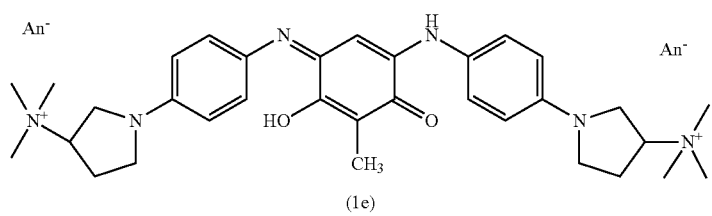
(1e)

Salt of 1-(4-{[-2-hydroxy-3-methyl-4-oxo-5-({4-[3-(trimethylammonio)pyrrolidin-1-yl]phenyl}amino)cyclohexa-2,5-diene-1-ylidene]amino}phenyl)-N,N,N-trimethylpyrrolidin-3-aminium

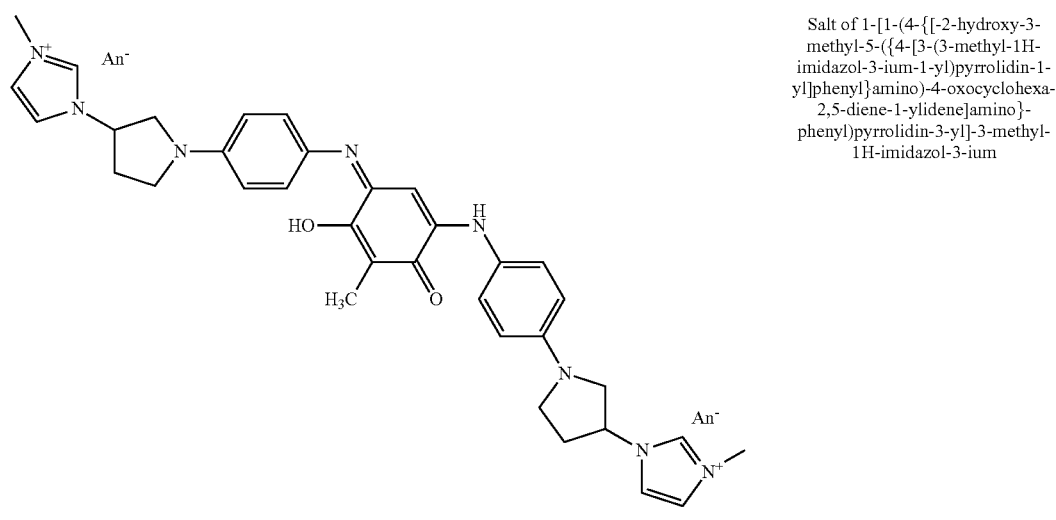

Salt of 1-[1-(4-{[-2-hydroxy-3-methyl-5-({4-[3-(3-methyl-1H-imidazol-3-ium-1-yl)pyrrolidin-1-yl]phenyl}amino)-4-oxocyclohexa-2,5-diene-1-ylidene]amino}-phenyl)pyrrolidin-3-yl]-3-methyl-1H-imidazol-3-ium (1f)

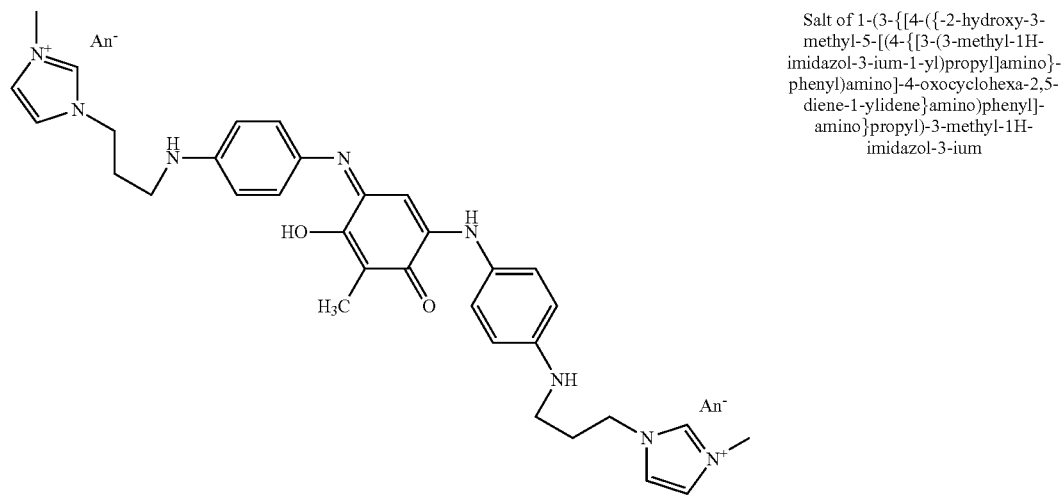

Salt of 1-(3-{[4-({-2-hydroxy-3-methyl-5-[(4-{[3-(3-methyl-1H-imidazol-3-ium-1-yl)propyl]amino}-phenyl)amino]-4-oxocyclohexa-2,5-diene-1-ylidene}amino)phenyl]-amino}propyl)-3-methyl-1H-imidazol-3-ium (1g)

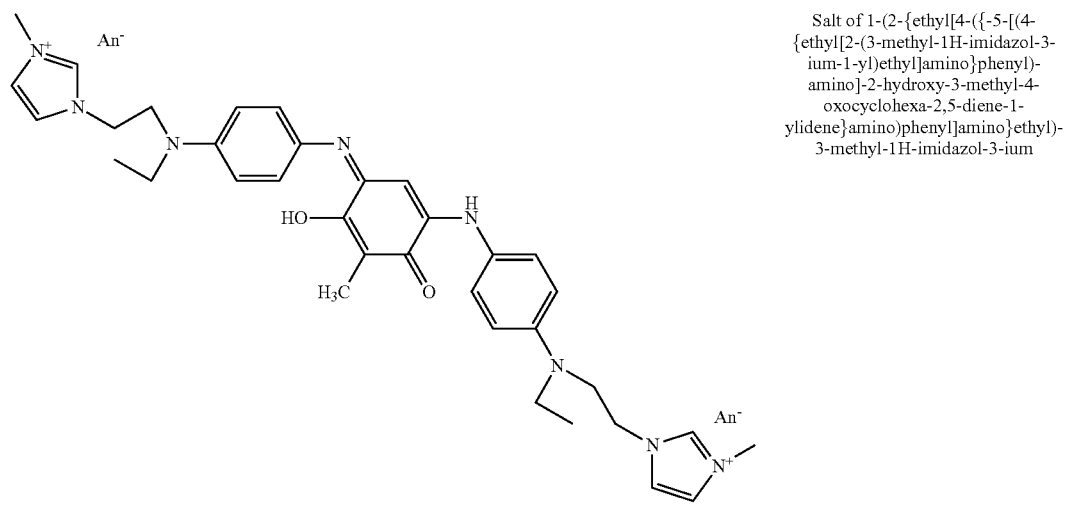

Salt of 1-(2-{ethyl[4-({-5-[(4-{ethyl[2-(3-methyl-1H-imidazol-3-ium-1-yl)ethyl]amino}phenyl)-amino]-2-hydroxy-3-methyl-4-oxocyclohexa-2,5-diene-1-ylidene}amino)phenyl]amino}ethyl)-3-methyl-1H-imidazol-3-ium (1h)

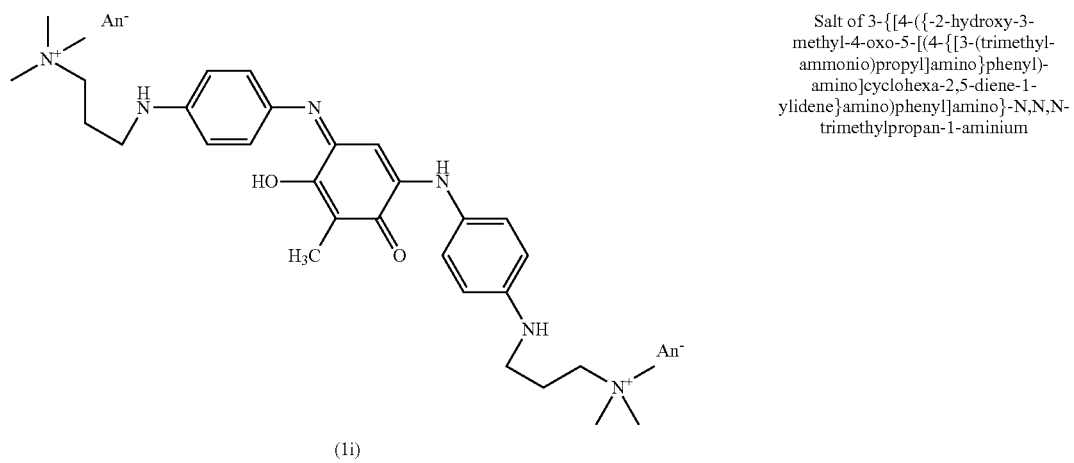

(1i)

Salt of 3-{[4-({-2-hydroxy-3-methyl-4-oxo-5-[(4-{[3-(trimethyl-ammonio)propyl]amino}phenyl)-amino]cyclohexa-2,5-diene-1-ylidene}amino)phenyl]amino}-N,N,N-trimethylpropan-1-aminium

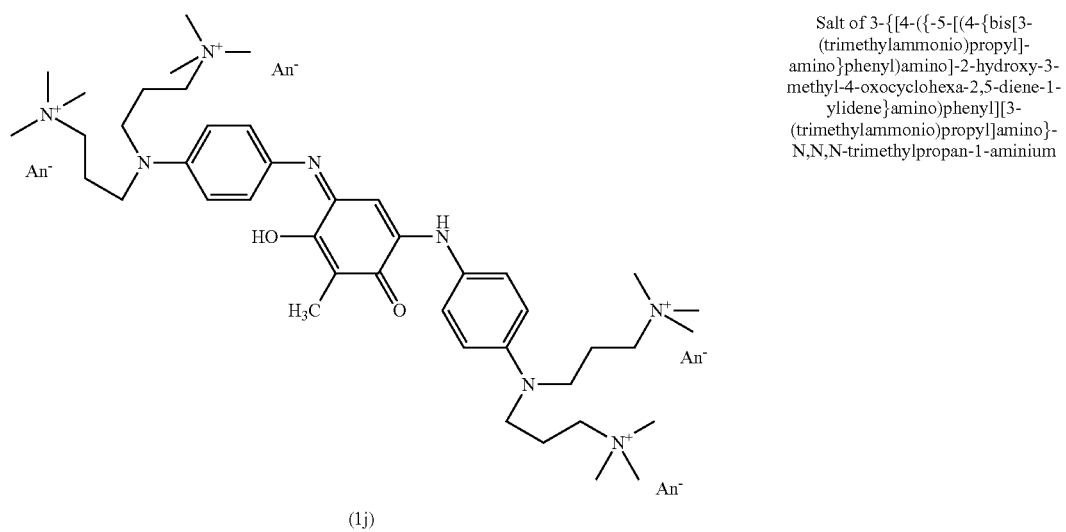

(1j)

Salt of 3-{[4-({-5-[(4-{bis[3-(trimethylammonio)propyl]-amino}phenyl)amino]-2-hydroxy-3-methyl-4-oxocyclohexa-2,5-diene-1-ylidene}amino)phenyl][3-(trimethylammonio)propyl]amino}-N,N,N-trimethylpropan-1-aminium

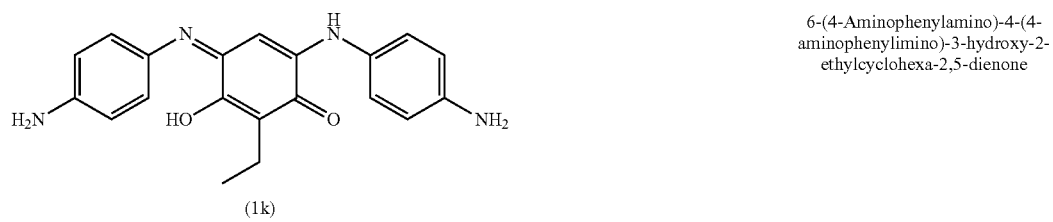

(1k)

6-(4-Aminophenylamino)-4-(4-aminophenylimino)-3-hydroxy-2-ethylcyclohexa-2,5-dienone

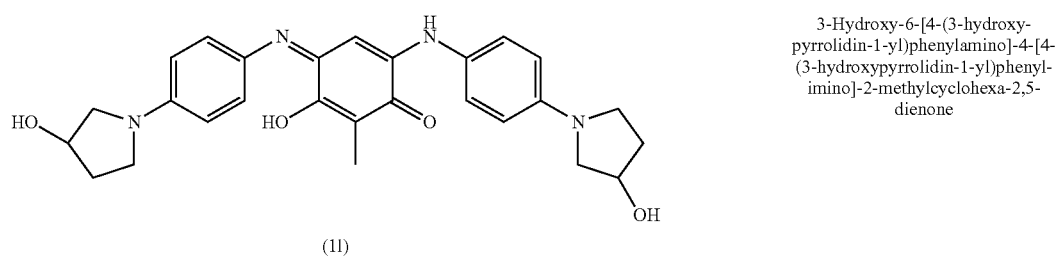

(1l)

3-Hydroxy-6-[4-(3-hydroxy-pyrrolidin-1-yl)phenylamino]-4-[4-(3-hydroxypyrrolidin-1-yl)phenyl-imino]-2-methylcyclohexa-2,5-dienone

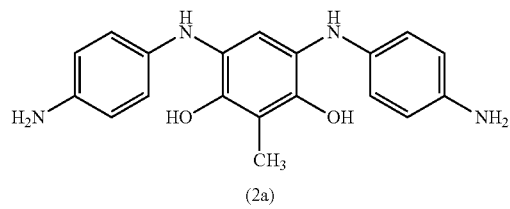
(2a)
4,6-Bis[(4-aminophenyl)amino]-2-methylbenzene-1,3-diol
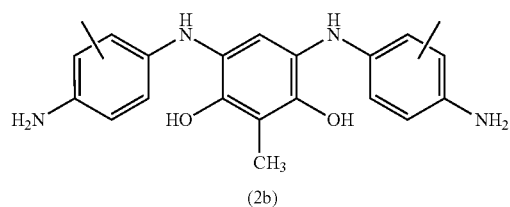
(2b)
4,6-Bis[(4-aminomethylphenyl)-amino]-2-methylbenzene-1,3-diol
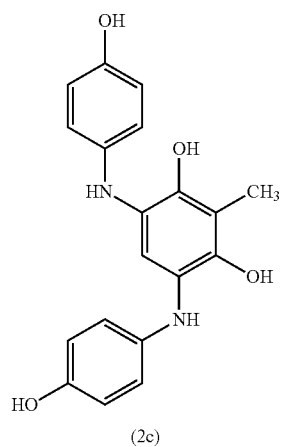
(2c)
4,6-Bis[(4-hydroxyphenyl)amino]-2-methylbenzene-1,3-diol
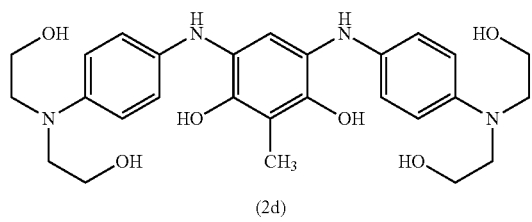
(2d)
4,6-Bis({4-[bis(2-hydroxyethyl)-amino]phenyl}amino)-2-methylbenzene-1,3-diol
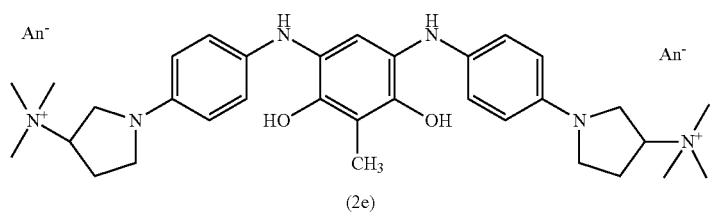
(2e)
Salt of 1,1'-[(4,6-dihydroxy-5-methyl-1,3-phenylene)bis(imino-4,1-phenylene)]bis(N,N,N-trimethylpyrrolidin-3-aminium)

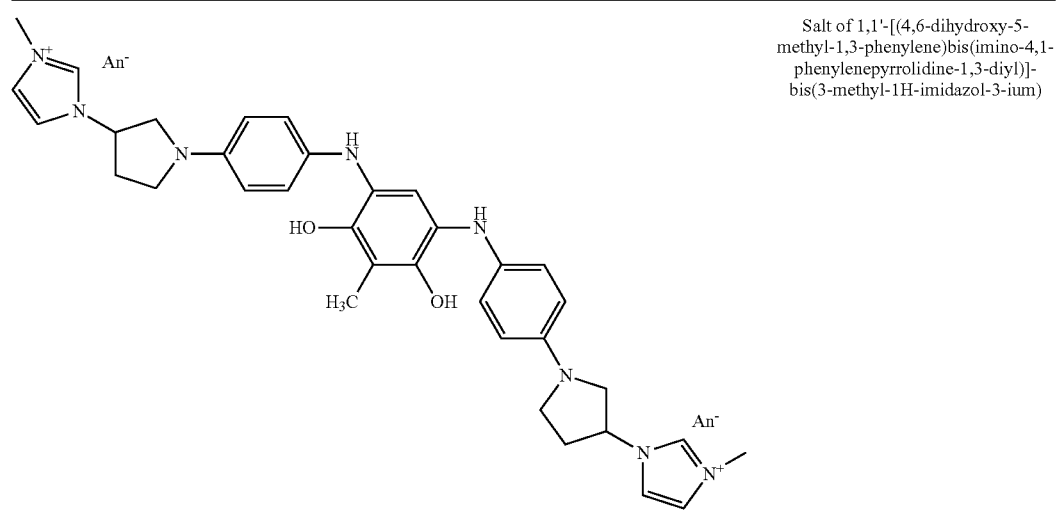
Salt of 1,1'-[(4,6-dihydroxy-5-methyl-1,3-phenylene)bis(imino-4,1-phenylenepyrrolidine-1,3-diyl)]-bis(3-methyl-1H-imidazol-3-ium)
(2f)
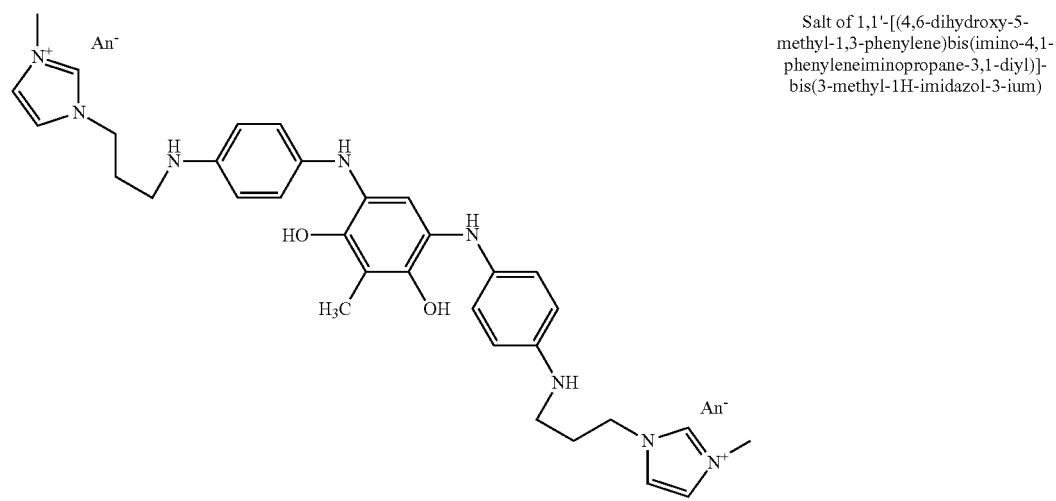
Salt of 1,1'-[(4,6-dihydroxy-5-methyl-1,3-phenylene)bis(imino-4,1-phenyleneiminopropane-3,1-diyl)]-bis(3-methyl-1H-imidazol-3-ium)
(2g)
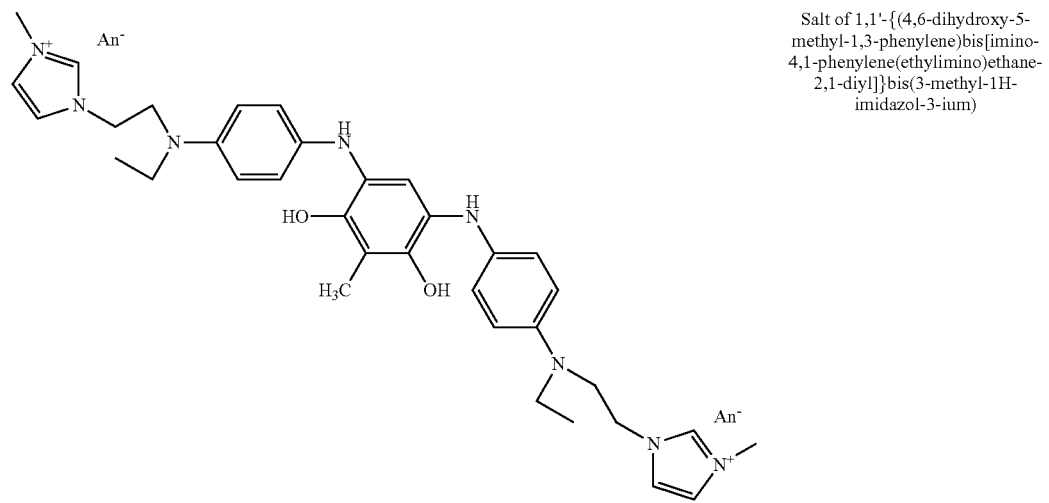
Salt of 1,1'-{(4,6-dihydroxy-5-methyl-1,3-phenylene)bis[imino-4,1-phenylene(ethylimino)ethane-2,1-diyl]}bis(3-methyl-1H-imidazol-3-ium)
(2h)

-continued
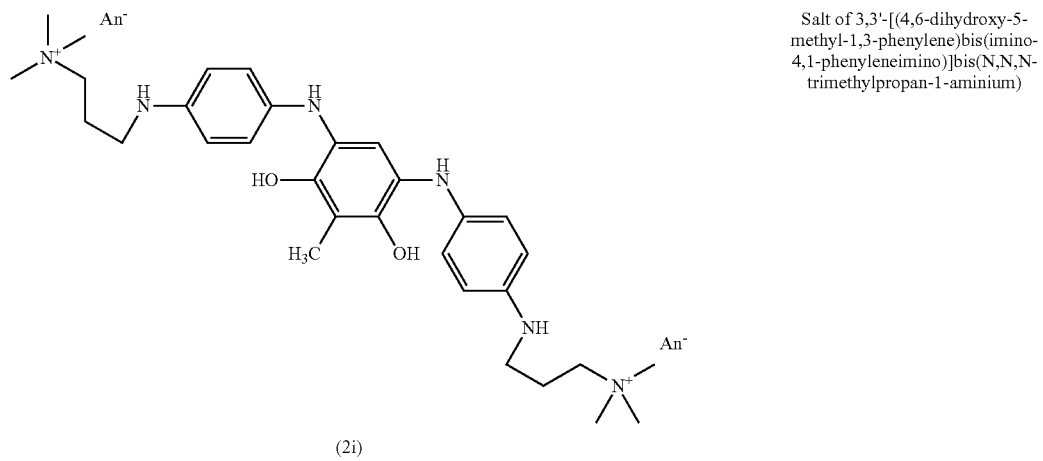
(2i) Salt of 3,3'-[(4,6-dihydroxy-5-methyl-1,3-phenylene)bis(imino-4,1-phenyleneimino)]bis(N,N,N-trimethylpropan-1-aminium)
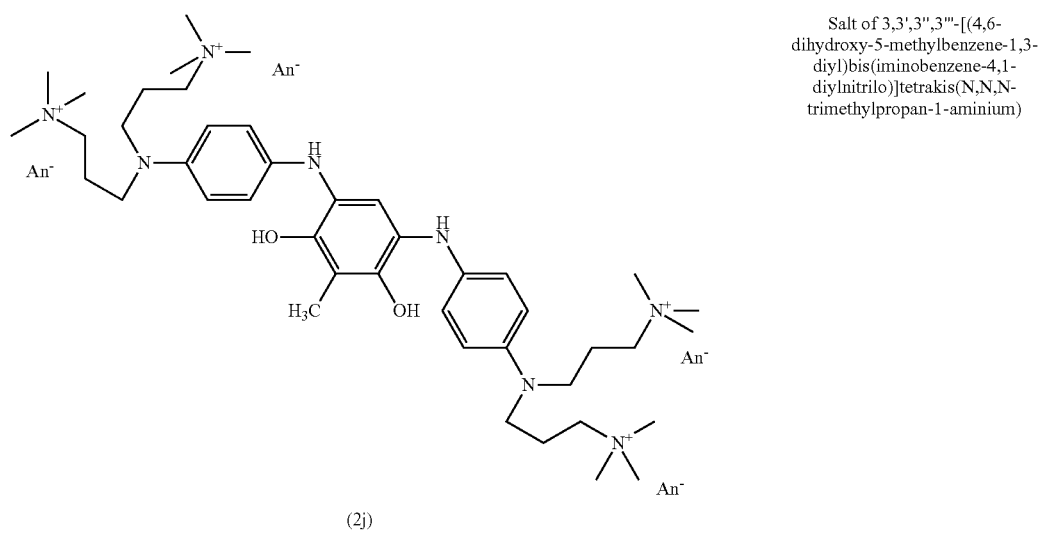
(2j) Salt of 3,3',3'',3'''-[(4,6-dihydroxy-5-methylbenzene-1,3-diyl)bis(iminobenzene-4,1-diylnitrilo)]tetrakis(N,N,N-trimethylpropan-1-aminium)
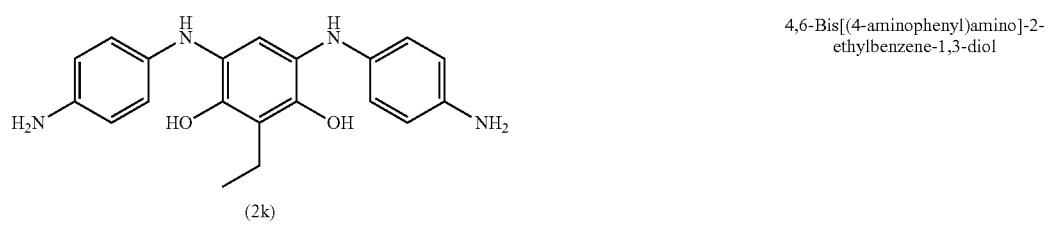
(2k) 4,6-Bis[(4-aminophenyl)amino]-2-ethylbenzene-1,3-diol
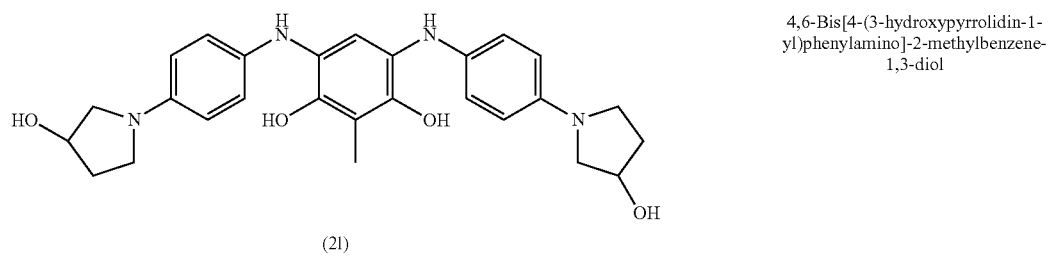
(2l) 4,6-Bis[4-(3-hydroxypyrrolidin-1-yl)phenylamino]-2-methylbenzene-1,3-diol with An⁻, which may be identical or different, representing an anionic counterion such as halide, An⁻ particularly representing a chloride.

More particularly, the dyes contained in the composition are chosen from the preceding dyes (1a), (1b), (1c), (1d), (1e), (1f), (1g) and (1i) and the salts thereof with an organic or mineral acid, geometrical isomers thereof, tautomers thereof and solvates thereof such as hydrates.

The compounds of formula (I) or (II) of the invention are prepared according to the following general synthetic routes:

1—Access to the Compounds Corresponding to Formula (I):

The compounds corresponding to formula (I) are generally obtained by reacting a 2-alkylresorcinol with a para-aminophenol derivative (X=OH) or a para-phenylenediamine derivative (X=—NR₃R₄), preferably in basic medium in the presence of an oxidizing agent. The base used is preferentially an aqueous solution of ammonia or of sodium hydroxide and the oxidizing agent is preferentially chosen from hydrogen peroxide, potassium ferricyanide, air, ammonium persulfate and manganese oxide.

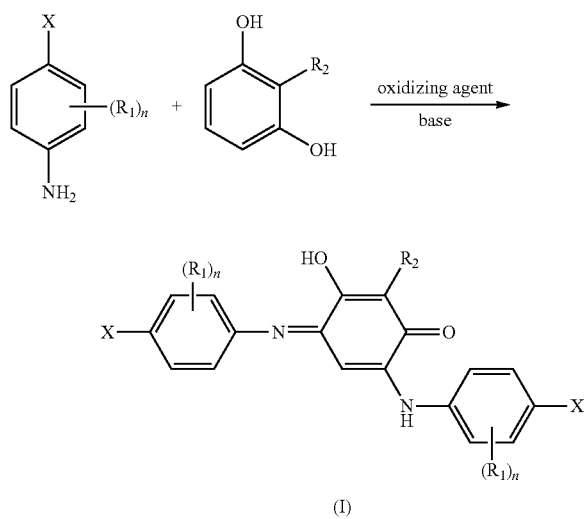

(I)

Similar synthetic approaches are described in patents FR 2 234 277, FR 2 047932, FR 2 106 661 and FR 2 121 101.

2—Access to the Compounds Corresponding to Formula (II):

The compounds corresponding to formula (II) are generally obtained by reacting the compounds of formula (I) with a reducing agent. This reducing agent is preferentially sodium hydrosulfite.

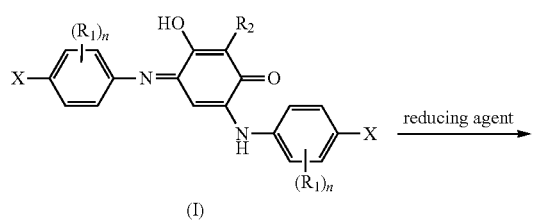

(I)

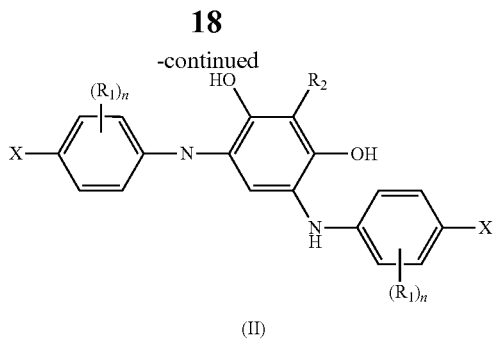

(II)

Similar synthetic approaches are described in patents FR 2 056 799, FR 2 047 932, FR 2 165 965 and FR 2 262 023.

The dye composition that is useful in the invention generally contains an amount of dye of formula (I) or of precursor of formula (II) of between 0.001% and 30% relative to the total weight of the composition. Preferably, this amount is between 0.005% and 10% by weight and even more preferentially between 0.01% and 6% by weight relative to the total weight of the composition.

The dye composition containing the dye of formula (I) or the precursor of formula (II), especially the precursor of formula (II), may also contain an oxidizing agent such as hydrogen peroxide, urea peroxide, alkali metal bromates, persalts, peracids and oxidase enzymes.

The dye composition may also contain additional direct dyes other than those of formula (I) or (II). These direct dyes are chosen, for example, from neutral, acidic or cationic nitrobenzene direct dyes, neutral, acidic or cationic azo direct dyes, tetraazapentamethine dyes, neutral, acidic or cationic quinone and in particular anthraquinone dyes, azine direct dyes, triarylmethane direct dyes, indoamine direct dyes and natural direct dyes.

Among the nitrobenzene direct dyes that may be mentioned, in a non-limiting manner, are the following compounds: 1,4-diamino-2-nitrobenzene, 1-amino-2-nitro-4-β-hydroxyethylaminobenzene, 1-amino-2-nitro-4-bis(β-hydroxyethyl)aminobenzene, 1,4-bis(β-hydroxyethylamino)-2-nitrobenzene, 1-β-hydroxyethylamino-2-nitro-4-bis(β-hydroxyethylamino)benzene, 1-β-hydroxyethylamino-2-nitro-4-aminobenzene, 1-β-hydroxyethylamino-2-nitro-4-(ethyl)(β-hydroxyethyl) aminobenzene, 1-amino-3-methyl-4-β-hydroxyethylamino-6-nitrobenzene, 1-amino-2-nitro-4-β-hydroxyethylamino-5-chlorobenzene, 1,2-diamino-4-nitrobenzene, 1-amino-2-β-hydroxyethylamino-5-nitrobenzene, 1,2-bis(β-hydroxyethylamino)-4-nitro-benzene, 1-amino-2-tris(hydroxymethyl)methylamino-5-nitrobenzene, 1-hydroxy-2-amino-5-nitrobenzene, 1-hydroxy-2-amino-4-nitrobenzene, 1-hydroxy-3-nitro-4-aminobenzene, 1-hydroxy-2-amino-4,6-dinitrobenzene, 1-β-hydroxyethyloxy-2-β-hydroxyethylamino-5-nitrobenzene, 1-methoxy-2-β-hydroxyethylamino-5-nitrobenzene, 1-β-hydroxyethyloxy-3-methylamino-4-nitrobenzene, 1-β,γ-dihydroxypropyloxy-3-methylamino-4-nitrobenzene, 1-β-hydroxyethylamino-4-β,γ-dihydroxypropyloxy-2-nitrobenzene, 1-β,γ-dihydroxypropylamino-4-trifluoromethyl-2-nitrobenzene, 1-β-hydroxyethylamino-4-trifluoro-methyl-2-nitrobenzene, 1-β-hydroxyethylamino-3-methyl-2-nitrobenzene, 1-β-aminoethylamino-5-methoxy-2-nitrobenzene, 1-hydroxy-2-chloro-6-ethylamino-4-nitrobenzene, 1-hydroxy-2-chloro-6-amino-4-nitrobenzene, 1-hydroxy-6-bis(β-hydroxyethyl)amino-3-nitrobenzene, 1-β-hydroxyethylamino-2-nitrobenzene, 1-hydroxy-4-β-hydroxyethylamino-3-nitrobenzene.

Among the azo direct dyes, mention may be made of the cationic azo dyes described in patent applications WO-95/15144, WO-95/01772 and EP-714 954, the content of which forms an integral part of the invention.

Among these compounds, mention may be made most particularly of the following dyes: 1,3-dimethyl-2-[[4-(dimethylamino)phenyl]azo]-1H-imidazolium chloride, 1,3-dimethyl-2-[(4-aminophenyl)azo]-1H-imidazolium chloride, 1-methyl-4-[(methylphenylhydrazono)methyl]-pyridinium methyl sulfate.

Among the azo direct dyes, mention may also be made of the following dyes, described in the COLOUR INDEX INTERNATIONAL 3rd edition:

Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Mention may also be made of 1-(4'-aminodiphenylazo)-2-methyl-4-bis($\beta$-hydroxyethyl)aminobenzene and 4-hydroxy-3-(2-methoxyphenylazo)-1-naphthalenesulfonic acid.

Among the quinone direct dyes, mention may be made of the following dyes:

Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds: 1-N-methylmorpholiniumpropylamino-4-hydroxy-anthraquinone, 1-aminopropylamino-4-methylaminoanthra-quinone, 1-aminopropylaminoanthraquinone, 5-$\beta$-hydroxy-ethyl-1,4-diaminoanthraquinone, 2-aminoethylamino-anthraquinone, 1,4-bis($\beta,\gamma$-dihydroxypropylamino)-anthraquinone.

Among the azine dyes, mention may be made of the following compounds:

Basic Blue 17 and Basic Red 2.

Among the triarylmethane dyes, mention may be made of the following compounds: Basic Green 1, Acid Blue 9, Basic Violet 3, Basic Violet 14, Basic Blue 7, Acid Violet 49, Basic Blue 26, Acid Blue 7.

Among the indoamine dyes, mention may be made of the following compounds:

2-$\beta$-hydroxyethylamino-5-[bis($\beta$-4'-hydroxyethyl)amino]-anilino-1,4-benzoquinone;

2-$\beta$-hydroxyethylamino-5-(2'-methoxy-4'-amino)anilino-1,4-benzoquinone;

3-N-(2'-chloro-4'-hydroxy)phenylacetylamino-6-methoxy-1,4-benzoquinoneimine;

3-N-(3'-chloro-4'-methylamino)phenylureido-6-methyl-1,4-benzoquinoneimine;

3-[4'-N-(ethyl,carbamylmethyl)amino]phenylureido-6-methyl-1,4-benzoquinoneimine.

Among the natural direct dyes, mention may be made of lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes, and especially henna-based poultices or extracts, may also be used.

The dye composition may contain one or more oxidation bases and/or one or more couplers conventionally used for the dyeing of keratin fibres.

Among the oxidation bases, mention may be made of para-phenylenediamines, bis(phenyl)alkylenediamines, para-aminophenols, bis-para-aminophenols, ortho-aminophenols and heterocyclic bases, and the addition salts thereof.

Among the couplers, mention may be made especially of meta-phenylenediamines, meta-aminophenols, meta-diphenols, naphthalene-based couplers and heterocyclic couplers, and the addition salts thereof.

The coupler(s) is (are) each generally present in an amount of between 0.001% and 10% by weight and preferably between 0.005% and 6% by weight relative to the total weight of the dye composition.

The oxidation base(s) present in the dye composition is (are) each generally present in an amount of between 0.001% and 10% by weight and preferably between 0.005% and 6% by weight relative to the total weight of the dye composition.

In general, the addition salts of the oxidation bases and couplers used in the context of the invention are especially chosen from the salts of addition with an acid, such as the hydrochlorides, hydrobromides, sulfates, citrates, succinates, tartrates, lactates, tosylates, benzenesulfonates, phosphates and acetates, and the salts of addition with a base, such as alkali metal hydroxides, for instance sodium hydroxide, potassium hydroxide, ammonia, amines or alkanolamines.

The medium that is suitable for dyeing, also known as the dye support, is a cosmetic medium generally comprising water or a mixture of water and of at least one organic solvent. Examples of organic solvents that may be mentioned include lower $C_1$-$C_4$ alkanols, such as ethanol and isopropanol; polyols and polyol ethers, for instance 2-butoxyethanol, propylene glycol, propylene glycol monomethyl ether and diethylene glycol monoethyl ether and monomethyl ether, and also aromatic alcohols, for instance benzyl alcohol or phenoxyethanol, and mixtures thereof.

When they are present, the solvents are preferably present in proportions preferably of between 1% and 50% by weight approximately, and even more preferentially between 5% and 40% by weight approximately, relative to the total weight of the dye composition.

The dye composition may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones such as amino silicones, film-forming agents, ceramides, preserving agents, opacifiers and conductive polymers.

The above adjuvants are generally present in an amount for each of them of between 0.01% and 20% by weight relative to the weight of the composition.

Needless to say, a person skilled in the art will take care to select this or these optional additional compound(s) such that the advantageous properties intrinsically associated with the dye composition in accordance with the invention are not, or are not substantially, adversely affected by the envisaged addition(s).

The pH of the dye composition is generally between 3 and 14 approximately. It may be adjusted to the desired value by means of acidifying or basifying agents usually used in the dyeing of keratin fibres, or alternatively using standard buffer systems.

According to one particular mode of the invention, when the dye composition comprises at least one dye of formula (I), the composition has a pH of between 6 and 11. According to another particular mode of the invention, when the composition comprises at least one dye precursor of formula (II), the composition has a pH of between 6 and 11.

Among the acidifying agents, examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

Among the basifying agents, examples that may be mentioned include aqueous ammonia, alkali metal carbonates, alkanolamines such as monoethanolamine, diethanolamine and triethanolamine, and also derivatives thereof, sodium hydroxide, potassium hydroxide and the compounds of formula (y) below:

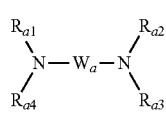

(Y)

in which $W_a$ is a propylene residue optionally substituted with a hydroxyl group or a $C_1$-$C_4$ alkyl radical; $R_{a1}$, $R_{a2}$, $R_{a3}$ and $R_{a4}$, which may be identical or different, represent a hydrogen atom or a $C_1$-$C_4$ alkyl or $C_1$-$C_4$ hydroxyalkyl radical.

The dye composition may be in various forms, such as in the form of a liquid, a cream or gel, or in any other form that is suitable for dyeing keratin fibres, and especially the hair.

Another subject of the invention is a process for dyeing keratin fibres, in particular the hair, which consists in applying to keratin materials, in the presence or absence of an oxidizing agent, a dye composition comprising, in a cosmetic medium, at least one azomethine dye of formula (I) or a dye precursor of formula (II) as defined previously.

After a leave-in time, the keratin fibres are rinsed to reveal dyed fibres. The leave-in time is generally between 3 and 50 minutes approximately and preferably 5 to 40 minutes approximately.

The application of the dye composition according to the invention is generally performed at room temperature. However, it may be performed at temperatures ranging from 20 to 80° C.

The examples that follow serve to illustrate the invention without, however, being limiting in nature. The dyes of the examples below were fully characterized via the standard spectroscopic and spectrometric methods.

EXAMPLES

Examples of Synthesis

Example 1

Synthesis of 6-(4-aminophenylamino)-4-(4-aminophenylimino)-3-hydroxy-2-methylcyclohexa-2,5-dienone 1 (Compound (1a))

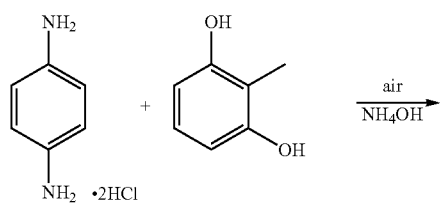

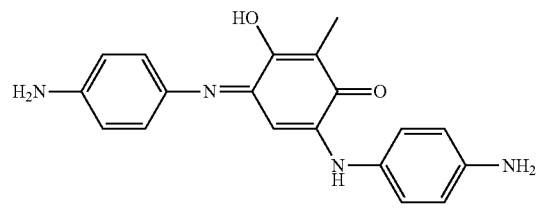

(Ia)

10 g (0.055 mol) of para-phenylenediamine, 3.43 g of 2-methylresorcinol and 330 ml of water are successively placed in a 1 liter round-bottomed flask with a mechanical stirrer and a sparging-air inlet. The pH is adjusted to 8.5 with 16 ml of 20% aqueous ammonia. The reaction medium is stirred for 48 hours and then filtered through a sinter funnel. The solid obtained is washed with water and then purified by chromatography on a column of silica (eluent: 80/20 dichloro-methane/methanol). 0.52 g of 6-(4-aminophenylamino)-4-(4-aminophenylimino)-3-hydroxy-2-methylcyclohexa-2,5-dienone (1a) is obtained.

Example 2

Synthesis of 6-(4-aminomethylphenylamino)-4-(4-aminomethylphenylimino)-3-hydroxy-2-methyl-cyclohexa-2,5-dienone 2 (Compound (1b))

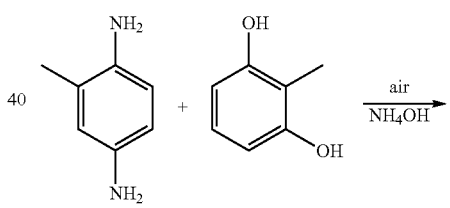

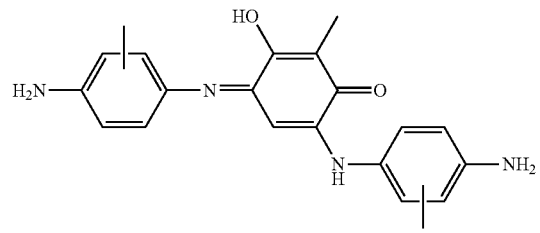

(1b)

39.02 g (0.2 mol) of para-toluenediamine, 14.02 g (0.1 mol) of 2-methylresorcinol and 600 ml of water are successively placed in a round-bottomed flask with a mechanical stirrer and a sparging-air inlet. The pH is adjusted to 9.5 with 70 ml of 20% aqueous ammonia. The reaction medium is stirred for 6 hours and then filtered through a sinter funnel. The solid obtained is washed with water and then purified by chromatography on a column of silica (eluent: 95/5 dichloromethane/methanol). 0.350 g of 6-(4-amino-methylphenylamino)-4-(4-aminomethylphenylimino)-3-hydroxy-2-methyl-cyclohexa-2,5-dienone (1b) is obtained.

Example 3

Synthesis of 3-hydroxy-6-(4-hydroxyphenyl-amino)-4-(4-hydroxyphenylimino)-2-methyl-cyclohexa-2,5-dienone 3 (Compound (1c))

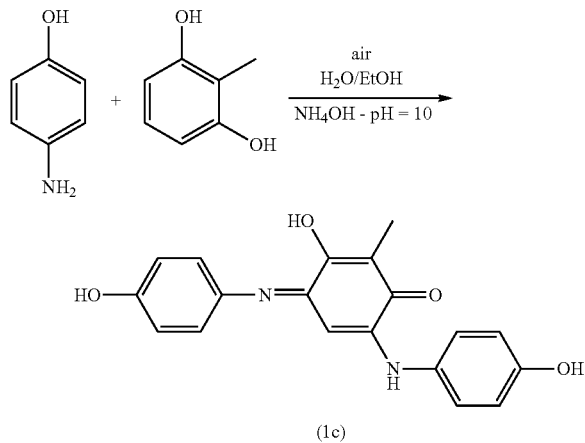

3 g (0.24 mol) of 2-methylresorcinol dissolved in 72 ml of ethanol are added to a solution containing 2.2 g (0.20 mol) of para-aminophenol dissolved in 72 ml of water in a round-bottomed flask with a mechanical stirrer and a sparging-air inlet. The pH is adjusted to with aqueous 20% ammonium hydroxide solution. The reaction medium is stirred for 24 hours and then filtered through a sinter funnel. The solid obtained is washed with water and is then crystallized when cold from methanol. The solid obtained is filtered off and washed with water and then dried. 0.240 g of 3-hydroxy-6-(4-hydroxyphenylamino)-4-(4-hydroxyphenylimino)-2-methylcyclohexa-2,5-dienone (1c) is obtained.

Example 4

Synthesis of 6-{4-[bis(2-hydroxyethyl)-amino]phenylamino}-4-{4-[bis(2-hydroxyethyl)-amino]phenylimino}-3-hydroxy-2-methyl-cyclohexa-2,5-dienone 4 (Compound (1d))

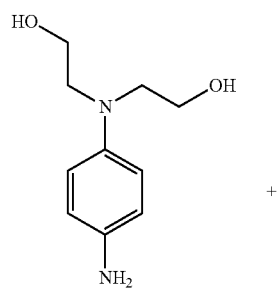

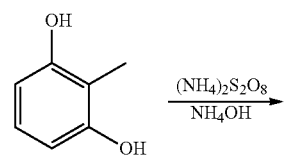

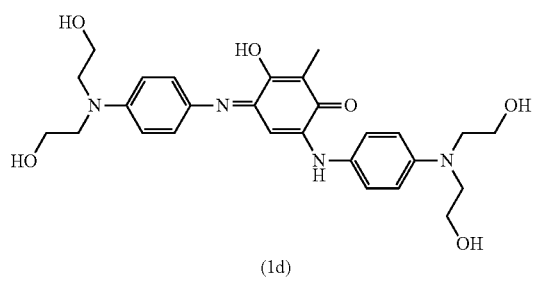

2.8 g (10 mmol) of 2-[(4-aminophenyl)(2-hydroxyethyl)-amino]ethanol and 0.62 g (5 mmol) of 2-methylresorcinol are added to a solution containing 30 ml of water and 10 ml of ethanol in a three-necked flask equipped with a thermometer, an addition funnel and a magnetic stirrer. The pH is adjusted to 9.8 with 20% aqueous ammonia.

The reaction medium is cooled to 5° C., and 3.42 g (15 mmol) of ammonium persulfate dissolved in 15 ml of water are then added, while keeping the temperature between 5° C. and 10° C. 10 ml of ethanol are then added and the mixture is stirred for 45 minutes. The solid formed is filtered off and then washed with water. 0.38 g of 6-{4-[bis(2-hydroxyethyl)amino]phenylamino}-4-{4-[bis(2-hydroxyethyl)amino]phenylimino}-3-hydroxy-2-methylcyclohexa-2,5-dienone (1d) is obtained.

Example 5

Synthesis of 4,6-bis[(4-aminophenyl)amino]-2-methylbenzene-1,3-diol (2a)

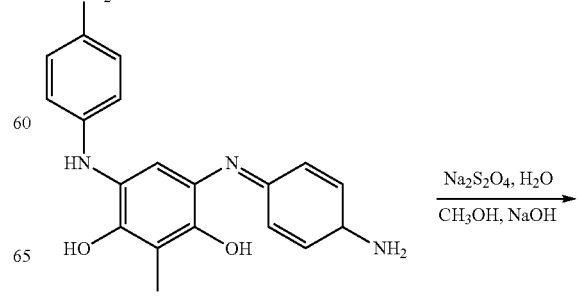

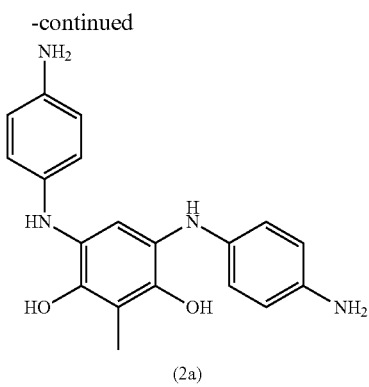

(2a)

10 mg (0.04 mol) of 6-[(4-aminophenyl)amino]-4-[(4-aminophenyl)imino]-3-hydroxy-2-methylcyclohexa-2,5-dien-1-one are added to a solution containing 16 mg sodium hydrosulfite in 500 μl of methanol and 5 μl of aqueous sodium hydroxide solution. The reaction medium is stirred and the solution is then worked up according to the usual procedure and characterized. 4,6-Bis[(4-aminophenyl)amino]-2-methylbenzene-1,3-diol (2a) is obtained.

Example 6

Synthesis of 4,6-bis[(4-amino-3-methyl-phenyl)amino]-2-methylbenzene-1,3-diol (2b)

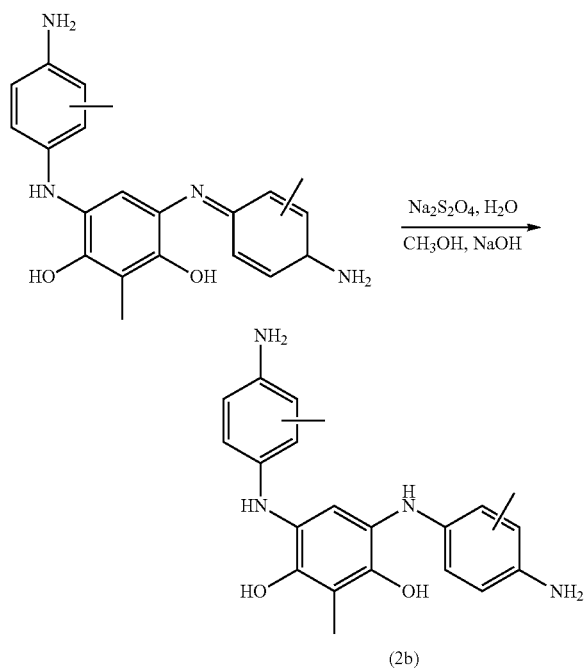

(2b)

10 mg (0.04 mol) of 6-[(4-amino-2-methylphenyl)amino]-4-[(4-amino-2-methylphenyl)imino]-3-hydroxy-2-methyl-cyclohexa-2,5-dien-1-one are added to a solution containing 16 mg of sodium hydrosulfite in 500 μl of methanol and 5 μl of aqueous sodium hydroxide solution. The reaction medium is stirred and the solution is then worked up according to the usual procedure and characterized. 4,6-Bis[(4-amino-3-methylphenyl)amino]-2-methylbenzene-1,3-diol (2b) is obtained.

Example 7

Synthesis of 4,6-bis({4-[bis(2-hydroxy-ethyl)amino]phenyl}amino)-2-methylbenzene-1,3-diol (2d)

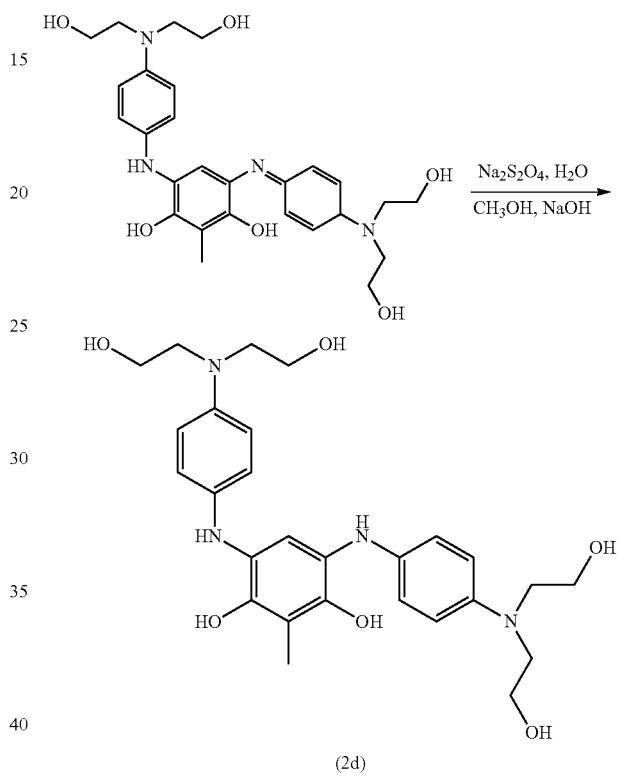

(2d)

13 mg (0.04 mol) of (4Z)-6-({4-[bis(2-hydroxyethyl)-amino]phenyl}amino)-4-({4-[bis(2-hydroxyethyl)amino]-phenyl}imino)-3-hydroxy-2-methylcyclohexa-2,5-dien-1-one are added to a solution containing 16 mg of sodium hydrosulfite in 500 μl of methanol and 5 μl of aqueous sodium hydroxide solution. The reaction medium is stirred and the solution is then worked up according to the usual procedure and characterized. 4,6-Bis({4-[bis(2-hydroxyethyl)amino]phenyl}amino)-2-methyl-benzene-1,3-diol is obtained.

Examples of Dyeing

Dyeing in Neutral Medium

The dye compositions (A) and (B) below are prepared from the dye compounds (1a) and (1b) synthesized previously.

| Composition | (A) | (B) |
|---|---|---|
| Compound (1a) | $10^{-3}$ mol | — |
| Compound (1b) | — | $10^{-3}$ mol |

| | | |
|---|---|---|
| Dye support (1) | (*) | (*) |
| Demineralized water qs | 100 g | 100 g |

(*): dye support (1) pH = 7 with the dye support constituted of:

| | |
|---|---|
| 96° ethyl alcohol | 20.8 g |
| Pentasodium salt of diethylenetriaminepenta-acetic acid as an aqueous 40% solution | 0.48 g AM |
| $C_8$-$C_{10}$ alkyl polyglucoside as an aqueous 60% solution | 3.6 g AM |
| Benzyl alcohol | 2.0 g |
| Polyethylene glycol containing 8 units of ethylene oxide | 3.0 g |
| $Na_2HPO_4$ | 0.28 g |
| $KH_2PO_4$ | 0.46 g |

Compositions (A) and (B) are applied to locks of grey hair containing 90% white hairs. After a leave-on time of 30 minutes, the locks are rinsed, washed with a standard shampoo, rinsed again and then dried.

The shades obtained are given in the table below:

| Composition | (A) | (B) |
|---|---|---|
| Shade obtained after treatment | Pale yellow | Pale orange |

Dyeing in Basic Medium

The dye compositions (C) and (D) below are prepared from compounds (1a) and (1b), respectively.

| Composition | (C) | (D) |
|---|---|---|
| Compound (1a) | $10^{-3}$ mol | — |
| Compound (1b) | — | $10^{-3}$ mol |
| Dye support (2) | (*) | (*) |
| Demineralized water qs | 100 g | 100 g |

(*): dye support (2) pH = 9.5 with the dye support constituted of:

| | |
|---|---|
| 96° ethyl alcohol | 20.8 g |
| Pentasodium salt of diethylenetriaminepenta-acetic acid as an aqueous 40% solution | 0.48 g AM |
| $C_8$-$C_{10}$ alkyl polyglucoside as an aqueous 60% solution | 3.6 g AM |
| Benzyl alcohol | 2.0 g |
| Polyethylene glycol containing 8 units of ethylene oxide | 3.0 g |
| $NH_4Cl$ | 4.32 g |
| Aqueous ammonia containing 20% $NH_3$ | 2.94 g |

Compositions (C) and (D) are applied to locks of grey hair containing 90% white hairs. After a leave-on time of 30 minutes, the locks are rinsed, washed with a standard shampoo, rinsed again and then dried.

The shades obtained are given in the table below:

| Composition | (C) | (D) |
|---|---|---|
| Shade obtained after treatment | Pale orange | Pale orange |

The invention claimed is:

1. A compound of formula (I) or (II):

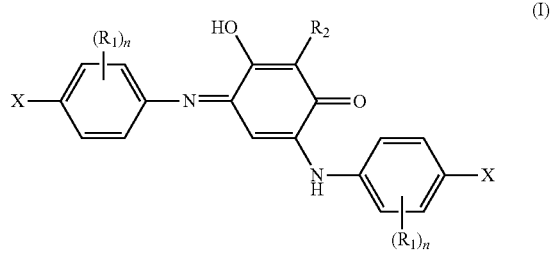

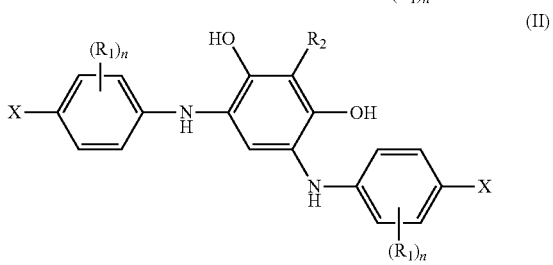

the salts thereof with an organic or mineral acid, geometrical isomers thereof, tautomers thereof, and solvates thereof including hydrates; in which formula (I) or (II):

$R_1$, which may be identical or different, represent:
  a chlorine atom;
  a ($C_1$-$C_3$) alkyl radical optionally substituted with one or more hydroxyl groups;
  a ($C_1$-$C_3$) alkoxy radical optionally substituted with one or more hydroxyl groups;

$R_2$ represents a ($C_1$-$C_3$) alkyl radical;

X, which may be identical or different, represent:
  a hydroxyl radical;
  a radical —$NR_3R_4$ with $R_3$ and $R_4$ representing, independently of each other:
    i) a hydrogen atom;
    ii) a $C_1$-$C_5$ alkyl radical optionally substituted with one or more groups chosen from hydroxyl, ($C_1$-$C_3$) alkoxy, amino, ($C_1$-$C_3$)alkylamino, di($C_1$-$C_3$) alkylamino, amino-carbonyl, carboxylic —COOH, sulfonic —$SO_3H$, tri($C_1$-$C_3$) alkylammonium and ($C_1$-$C_3$)alkyl-imidazolium;
  a pyrrolidinyl radical optionally substituted with a group chosen from hydroxyl, ($C_1$-$C_3$)alkoxy, amino, ($C_1$-$C_3$)alkylamino, di ($C_1$-$C_3$)alkylamino, tri($C_1$-$C_3$) alkylammonium and ($C_1$-$C_3$) alkylimidazolium;
  a piperidine radical optionally substituted with a group chosen from hydroxyl, ($C_1$-$C_3$)alkoxy, amino, ($C_1$-$C_3$)alkylamino, di($C_1$-$C_3$)alkylamino, tri($C_1$-$C_3$) alkylammonium and ($C_1$-$C_3$)alkylimid-azolium and;

n represents an integer between 0 and 3 inclusive;

with the proviso that when X and/or $R_3$ and/or $R_4$ comprise a cationic group, the electrical neutrality of the compound of formula (I) or (II) is achieved with an anionic counterion or a mixture of anionic counterions that are cosmetically acceptable, including chlorides, bromides and sulfates.

2. A compound of formula (I) or (II) according to the claim 1, for which n is zero.

3. A compound of formula (I) or (II) according to claim 1, for which n is 1 and $R_1$ represents a ($C_1$-$C_3$)alkyl radical.

4. Compound of formula (I) or (II) according to claims 1, 2, or 3, for which X represents a hydroxyl radical.

5. A compound of formula (I) or (II) according to any one of claims 1 to 3, for which X represents a radical —NR$_3$R$_4$ with R$_3$ and R$_4$ representing, independently of each other, i) a hydrogen atom or ii) a C$_1$-C$_5$ alkyl radical optionally substituted with one or more groups chosen from hydroxyl, (C$_1$-C$_3$)alkoxy, amino, (C$_1$-C$_3$)alkyl-amino, di(C$_1$-C$_3$)alkylamino, aminocarbonyl, carboxylic, sulfonic —, tri(C$_1$-C$_3$)alkylammonium and (C$_1$-C$_3$)alkylimidazolium.

6. A compound of formula (I) or (II) according to any one of claims 1, 2, or 3, for which X represents a pyrrolidinyl group optionally substituted with a tri (C$_1$-C$_3$) alkylammonium or (C$_1$-C$_3$) alkylimidazolium group.

7. A compound of formula (I) or (II) according claims 1 which is chosen from the following compounds:

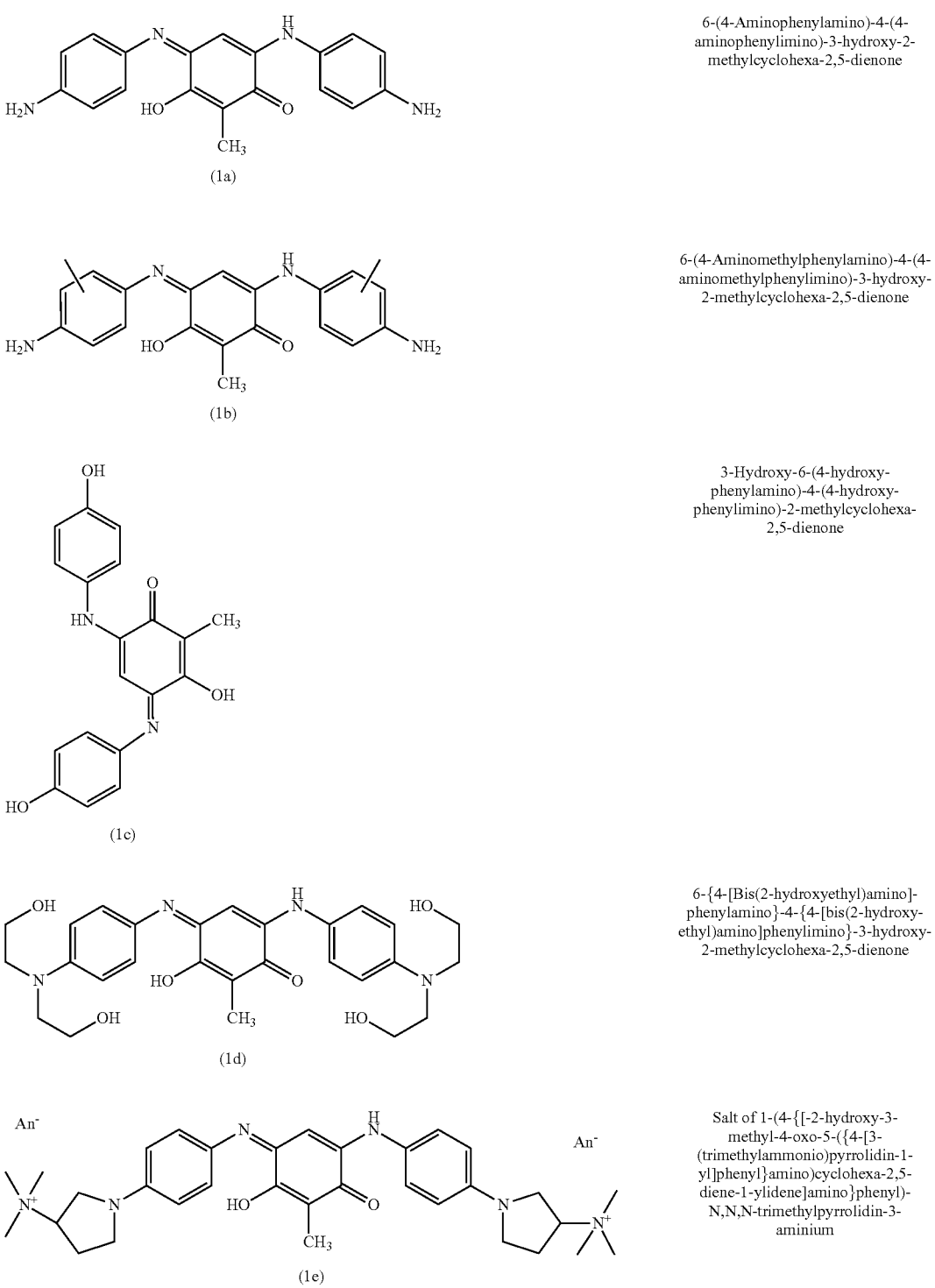

6-(4-Aminophenylamino)-4-(4-aminophenylimino)-3-hydroxy-2-methylcyclohexa-2,5-dienone (1a)

6-(4-Aminomethylphenylamino)-4-(4-aminomethylphenylimino)-3-hydroxy-2-methylcyclohexa-2,5-dienone (1b)

3-Hydroxy-6-(4-hydroxyphenylamino)-4-(4-hydroxyphenylimino)-2-methylcyclohexa-2,5-dienone (1c)

6-{4-[Bis(2-hydroxyethyl)amino]-phenylamino}-4-{4-[bis(2-hydroxyethyl)amino]phenylimino}-3-hydroxy-2-methylcyclohexa-2,5-dienone (1d)

Salt of 1-(4-{[-2-hydroxy-3-methyl-4-oxo-5-({4-[3-(trimethylammonio)pyrrolidin-1-yl]phenyl}amino)cyclohexa-2,5-diene-1-ylidene]amino}phenyl)-N,N,N-trimethylpyrrolidin-3-aminium (1e)

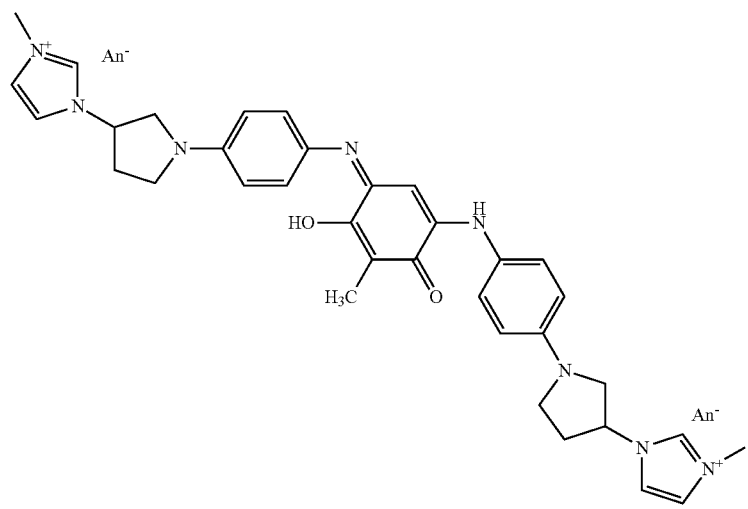

Salt of 1-[1-(4-{[-2-hydroxy-3-methyl-5-({4-[3-(3-methyl-1H-imidazol-3-ium-1-yl)pyrrolidin-1-yl]phenyl}amino)-4-oxocyclohexa-2,5-diene-1-ylidene]amino}-phenyl)pyrrolidin-3-yl]-3-methyl-1H-imidazol-3-ium (1f)

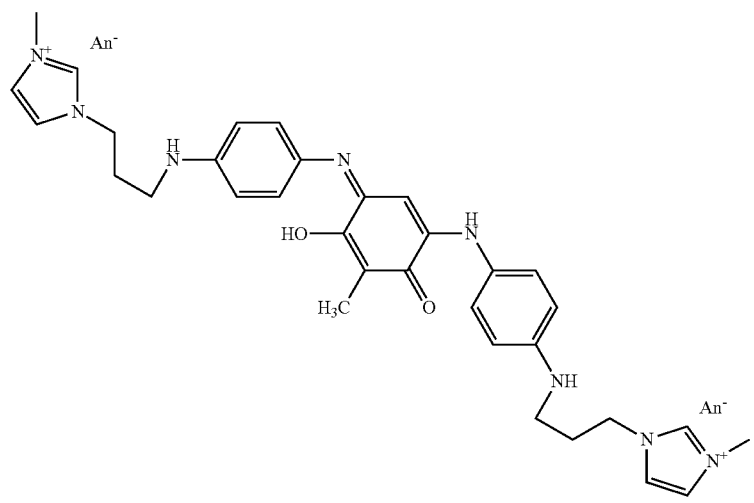

Salt of 1-(3-{[4-({-2-hydroxy-3-methyl-5-[(4-{[3-(3-methyl-1H-imidazol-3-ium-1-yl)propyl]amino}-phenyl)amino]-4-oxocyclohexa-2,5-diene-1-ylidene}amino)phenyl]-amino}propyl)-3-methyl-1H-imidazol-3-ium (1g)

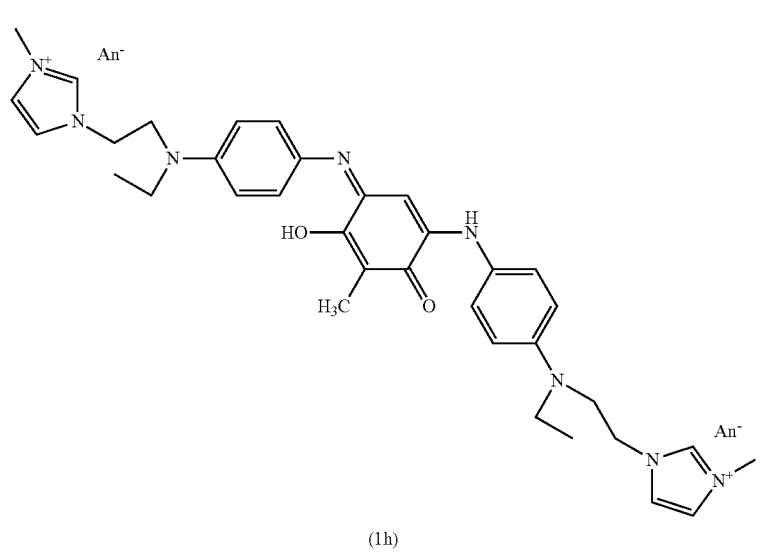

Salt of 1-(2-{ethyl[4-({-5-[(4-{ethyl[2-(3-methyl-1H-imidazol-3-ium-1-yl)ethyl]amino}phenyl)-amino]-2-hydroxy-3-methyl-4-oxocyclohexa-2,5-diene-1-ylidene}amino)phenyl]amino}ethyl)-3-methyl-1H-imidazol-3-ium (1h)

-continued

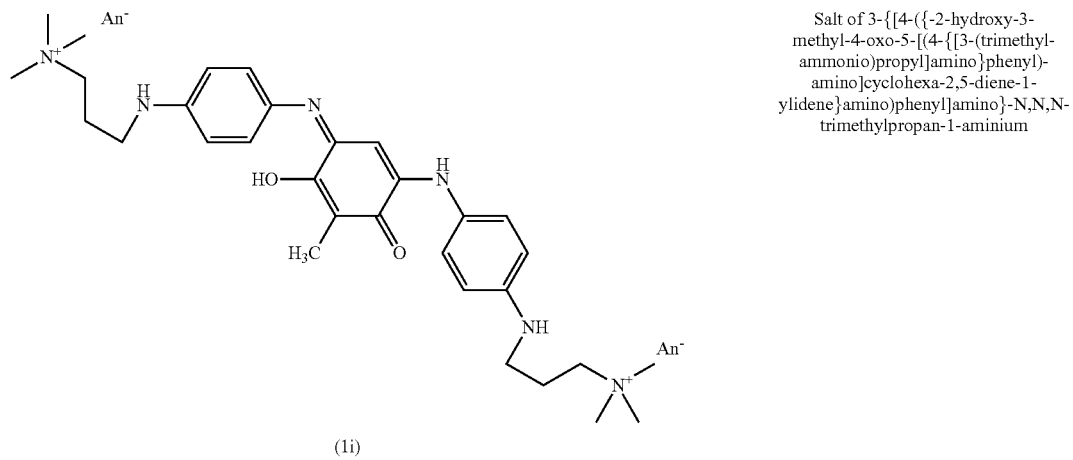

(1i)

Salt of 3-{[4-({-2-hydroxy-3-methyl-4-oxo-5-[(4-{[3-(trimethyl-ammonio)propyl]amino}phenyl)-amino]cyclohexa-2,5-diene-1-ylidene}amino)phenyl]amino}-N,N,N-trimethylpropan-1-aminium

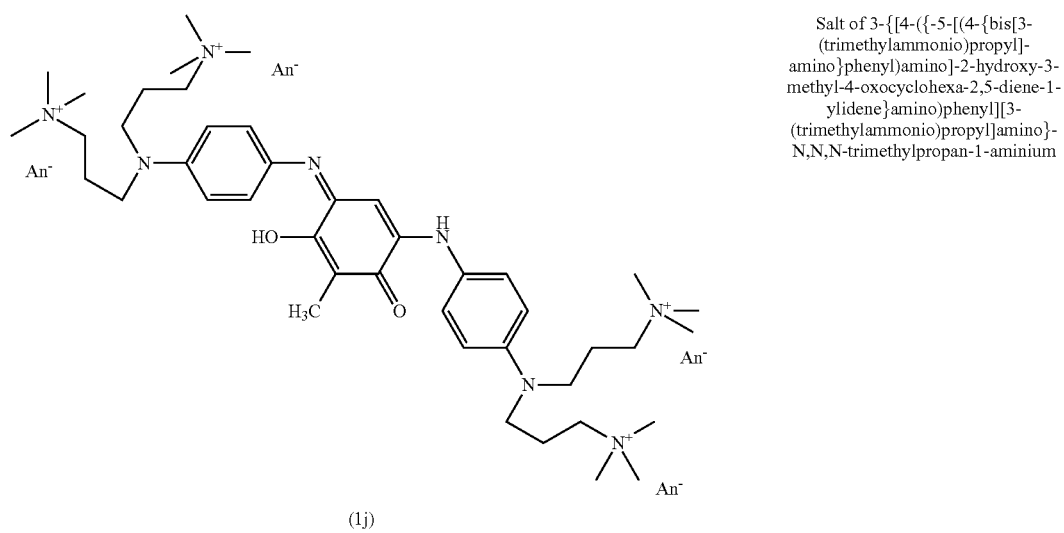

(1j)

Salt of 3-{[4-({-5-[(4-{bis[3-(trimethylammonio)propyl]-amino}phenyl)amino]-2-hydroxy-3-methyl-4-oxocyclohexa-2,5-diene-1-ylidene}amino)phenyl][3-(trimethylammonio)propyl]amino}-N,N,N-trimethylpropan-1-aminium

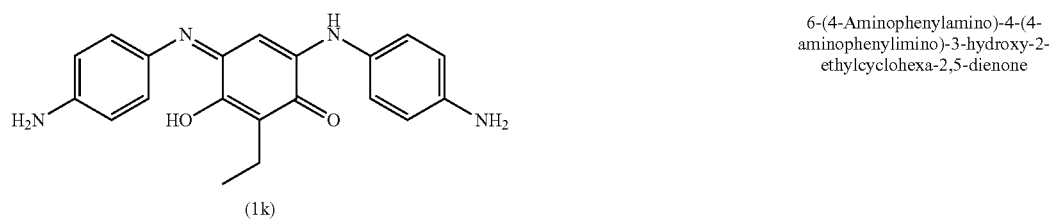

(1k)

6-(4-Aminophenylamino)-4-(4-aminophenylimino)-3-hydroxy-2-ethylcyclohexa-2,5-dienone

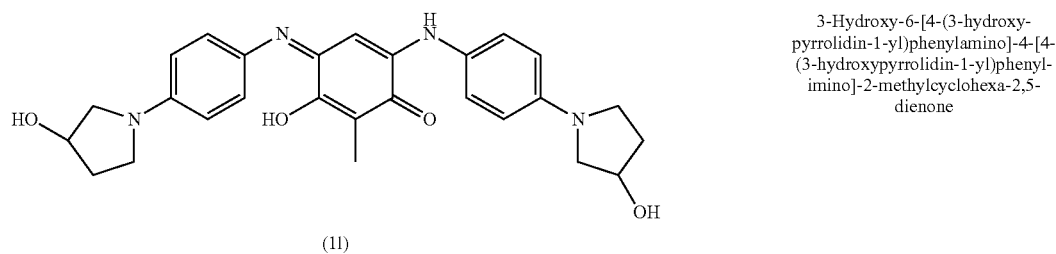

(1l)

3-Hydroxy-6-[4-(3-hydroxy-pyrrolidin-1-yl)phenylamino]-4-[4-(3-hydroxypyrrolidin-1-yl)phenyl-imino]-2-methylcyclohexa-2,5-dienone

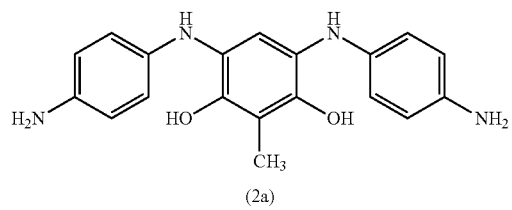
4,6-Bis[(4-aminophenyl)amino]-2-methylbenzene-1,3-diol
(2a)
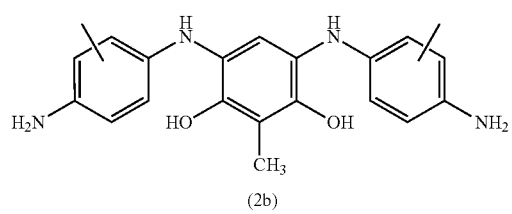
4,6-Bis[(4-aminomethylphenyl)-amino]-2-methylbenzene-1,3-diol
(2b)
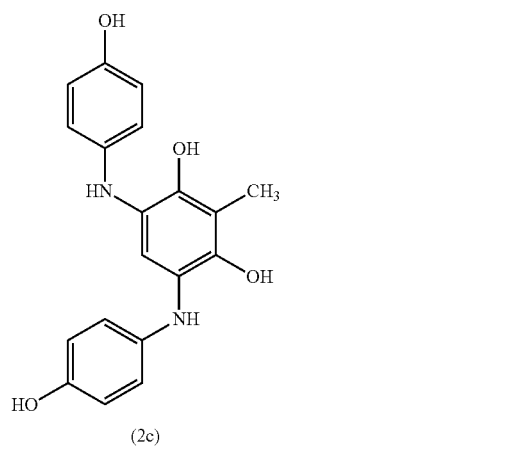
4,6-Bis[(4-hydroxyphenyl)amino]-2-methylbenzene-1,3-diol
(2c)
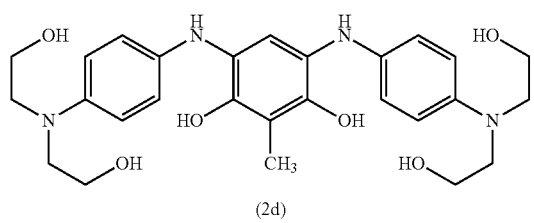
4,6-Bis({4-[bis(2-hydroxyethyl)-amino]phenyl}amino)-2-methylbenzene-1,3-diol
(2d)
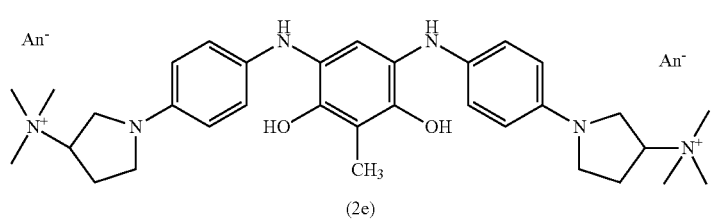
Salt of 1,1'-[(4,6-dihydroxy-5-methyl-1,3-phenylene)bis(imino-4,1-phenylene)]bis(N,N,N-trimethylpyrrolidin-3-aminium)
(2e)

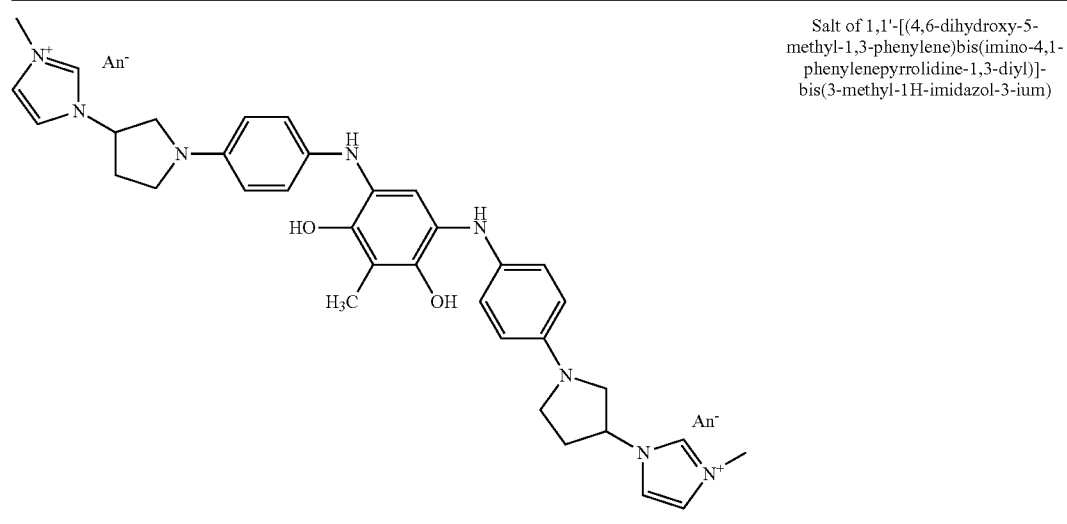
Salt of 1,1'-[(4,6-dihydroxy-5-methyl-1,3-phenylene)bis(imino-4,1-phenylenepyrrolidine-1,3-diyl)]-bis(3-methyl-1H-imidazol-3-ium)
(2f)
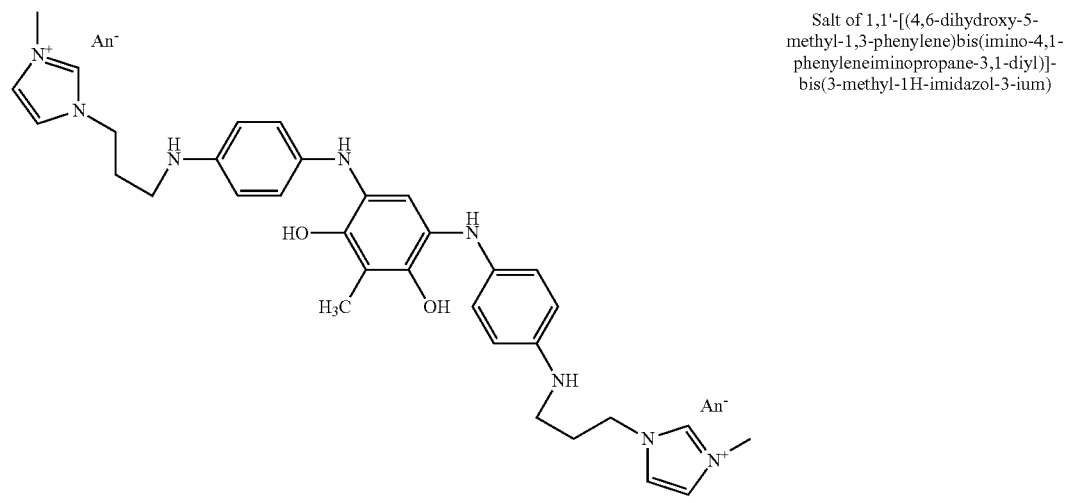
Salt of 1,1'-[(4,6-dihydroxy-5-methyl-1,3-phenylene)bis(imino-4,1-phenyleneiminopropane-3,1-diyl)]-bis(3-methyl-1H-imidazol-3-ium)
(2g)
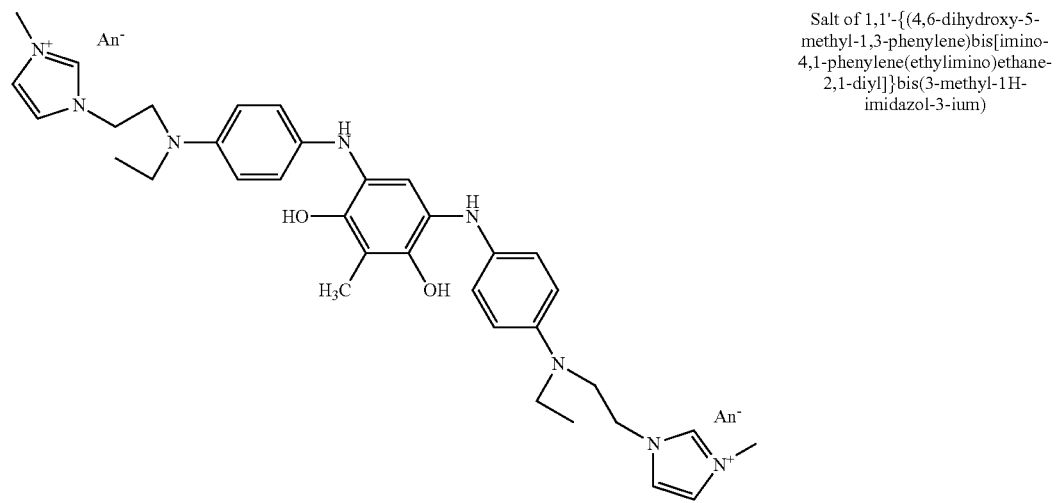
Salt of 1,1'-{(4,6-dihydroxy-5-methyl-1,3-phenylene)bis[imino-4,1-phenylene(ethylimino)ethane-2,1-diyl]}bis(3-methyl-1H-imidazol-3-ium)
(2h)

-continued
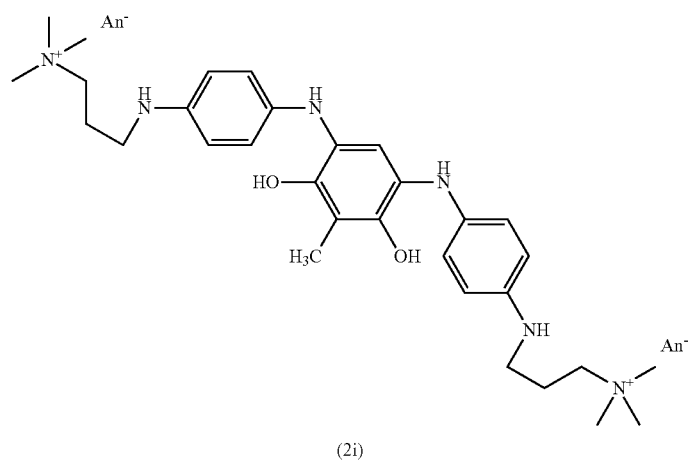
(2i)
Salt of 3,3'-[(4,6-dihydroxy-5-methyl-1,3-phenylene)bis(imino-4,1-phenyleneimino)]bis(N,N,N-trimethylpropan-1-aminium)
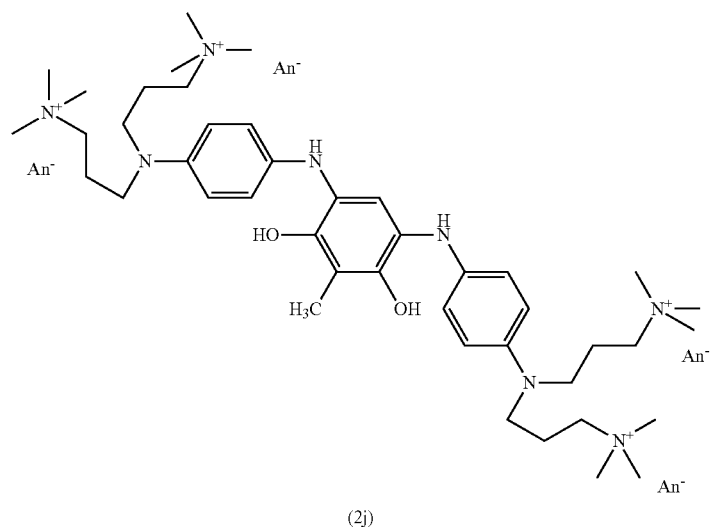
(2j)
Salt of 3,3',3'',3'''-[(4,6'-dihydroxy-5-methylbenzene-1,-3-diyl)bis(iminobenzene-4,-1-diylnitrilo)]tetrakis(N,N,N-trimethylpropan-1-aminium)
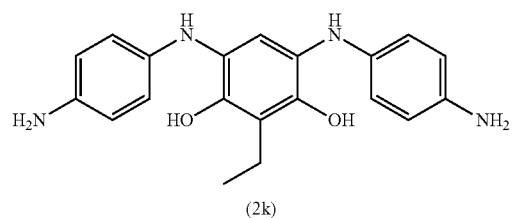
(2k)
4,6-Bis[(4-aminophenyl)amino]-2-ethylbenzene-1,3-diol
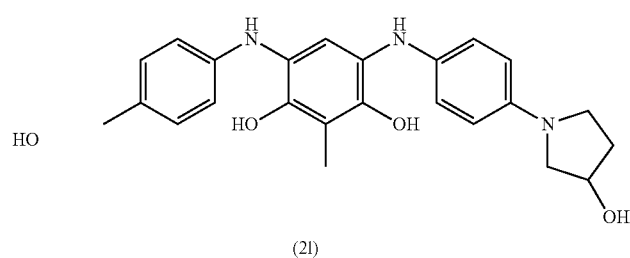
(2l)
4,6-Bis[4-(3-hydroxypyrrolidin-1-yl)phenylamino]-2-methylbenzene-1,3-diol wherein An⁻, which may be identical or different, represents an anionic counterion.

8. A dye composition comprising, in a suitable cosmetic medium, at least one compound of formula (I) or (II) according to claim 1.

9. The composition of claim 8, wherein the compound of formula (I) or (II) is present in an amount of between 0.001% and 30% by weight relative to the total weight of the composition.

10. The composition of claim 8 wherein the composition has a pH of between 6 and 11.

11. The composition of claim 9, wherein the composition has a pH of between 6 and 11.

12. The composition of claim 8 further comprising at least one oxidizing agent.

13. The composition claim 12, wherein the oxidizing agent is chosen from hydrogen peroxide, urea peroxide, alkali metal bromates, persalts, peracids and oxidase enzymes.

14. The composition of claim 8 further comprising at least one adjuvant chosen from anionic, cationic, nonionic, amphoteric and zwitterionic surfactants or mixtures thereof, anionic, cationic, nonionic, amphoteric or zwitterionic polymers or mixtures thereof, mineral or organic thickeners, antioxidants, penetrants, sequestrants, fragrances, buffers, dispersants, conditioning agents, film-forming agents, ceramides, preserving agents, opacifiers and conductive polymers.

15. A process for dyeing keratin fiber, comprising applying a dye composition according to claim 8 to the deratin fibers.

16. A process for dyeing keratin fibers, comprising applying at least a compound of formula (I) or (II) according to claim 1 to the keratin fibers.

17. A dye composition, in a suitable cosmetic medium, comprising at least one compound of formula (I) or (II) according to claim 7.

18. A process for dyeing keratin fibers, comprising applying a dye composition according to claim 17 to the keratin fibers.

19. A process for dyeing keratin fibers, comprising applying at least a compound of formula (I) or (II) according to claim 7 to the keratin fibers.

* * * * *

UNITED STATES PATENT AND TRADEMARK OFFICE
CERTIFICATE OF CORRECTION

PATENT NO. : 8,066,782 B2
APPLICATION NO. : 12/808134
DATED : November 29, 2011
INVENTOR(S) : Madeleine Leduc et al.

Page 1 of 1

It is certified that error appears in the above-identified patent and that said Letters Patent is hereby corrected as shown below:

Claim 1, col. 28, line 55, "and;" should read --; and--.

Claim 7, col. 30, line 5, "claims 1" should read --claim 1--.

Claim 15, col. 42, line 8, "deratin" should read --keratin--.

Signed and Sealed this
Eighteenth Day of September, 2012

David J. Kappos
*Director of the United States Patent and Trademark Office*